US006994998B1

(12) United States Patent
Stanton, Jr. et al.

(10) Patent No.: US 6,994,998 B1
(45) Date of Patent: *Feb. 7, 2006

(54) BASE-MODIFIED NUCLEOTIDES AND THEIR USE FOR POLYMORPHISM DETECTION

(75) Inventors: Vincent P. Stanton, Jr., Belmont, MA (US); Jia Liu Wolfe, Winchester, MA (US); Tomohiko Kawate, Cambridge, MA (US); Charles Allerson, Cambridge, MA (US); Gregory L. Verdine, Cambridge, MA (US)

(73) Assignee: Sequenom, Inc., San Diego, CA (US)

( * ) Notice: Subject to any disclaimer, the term of this patent is extended or adjusted under 35 U.S.C. 154(b) by 573 days.

This patent is subject to a terminal disclaimer.

(21) Appl. No.: 10/043,615

(22) Filed: Jan. 8, 2002

Related U.S. Application Data

(63) Continuation-in-part of application No. 09/394,467, filed on Sep. 10, 1999, now Pat. No. 6,566,059.

(60) Provisional application No. 60/102,724, filed on Oct. 1, 1998.

(51) Int. Cl.
*C12P 19/34* (2006.01)
*C12Q 1/68* (2006.01)
*C07H 21/00* (2006.01)
*C07H 21/02* (2006.01)
*C07H 21/04* (2006.01)

(52) U.S. Cl. .......... 435/91.1; 435/6; 435/91.2; 536/22.1; 536/23.1; 536/24.3; 536/25.3

(58) Field of Classification Search .......... 435/6, 435/91.1, 91.2; 536/22.1, 23.1, 24.3, 25.3
See application file for complete search history.

(56) References Cited

U.S. PATENT DOCUMENTS

| | | | |
|---|---|---|---|
| 4,701,419 A | 10/1987 | Morris | 436/89 |
| 4,879,214 A | 11/1989 | Kornher et al. | 435/91 |
| 5,003,059 A | 3/1991 | Brennan | 536/27 |
| 5,064,754 A | 11/1991 | Mills | 435/6 |
| 5,174,962 A | 12/1992 | Brennan | 422/78 |
| 5,187,085 A | 2/1993 | Lee | 435/91 |
| 5,221,518 A | 6/1993 | Mills | 422/62 |
| 5,332,666 A | 7/1994 | Prober et al. | 435/91.5 |
| 5,424,184 A | 6/1995 | Santamaria et al. | 435/6 |
| 5,547,835 A | 8/1996 | Köster | 435/6 |
| 5,552,278 A | 9/1996 | Brenner | 435/6 |
| 5,580,733 A | 12/1996 | Levis et al. | 435/6 |
| 5,605,798 A | 2/1997 | Köster | 435/6 |
| 5,622,824 A | 4/1997 | Köster | 435/6 |
| 5,691,141 A | 11/1997 | Köster | 435/6 |
| 5,700,642 A | 12/1997 | Monforte et al. | 435/6 |
| 5,830,655 A | 11/1998 | Monforte et al. | 435/6 |
| 5,869,242 A | 2/1999 | Kamb | 435/6 |
| 5,939,292 A | 8/1999 | Gelfand et al. | 435/91.2 |
| 6,566,059 B1 * | 5/2003 | Stanton et al. | 435/6 |

FOREIGN PATENT DOCUMENTS

| | | |
|---|---|---|
| WO | WO98/00433 | 1/1998 |

OTHER PUBLICATIONS

Andersson, B. et al., "Simultaneous shotgun sequencing of multiple cDNA clones," *DNA Sequence*, 1997, 7:63-70.

Astatke, M., et al, "Deoxynucleoside triphosphate and pyrophosphate binding sites in the catalytically competent ternary complex for the polymerase reaction catalyzed by DNA polymerase I (Klenow fragment)," *J. Biol. Chem.*, 1995, 270: 1945-54.

Astatke, M., et al, "How *E. coli* DNA polymerase I (Klenow fragment) distinguishes between Deoxy-and Dideoxynucleotides," *J. Mol. Biol.*, 1998, 278:147-165.

Astatke, M., et al, "A single side chain prevents *Escherichia coli* DNA polymerase I (Klenow fragment) from incorporating ribonucleotides," *Proc. Nat. Acad. Sci. USA*, 1998, 95:3402-3407.

Barnes, W.M., "DNA Sequencing by Partial Ribosubstitution," *J. Mol.Bio.*, 1978, 119:83-99.

Barnes, W.M., "PCR amplification of up to 35-kb DNA with high fidelity and high yield from λ bacteriophage templates," *Proc. Natl. Acad. Sci.* USA, 1994, 91:2216-2220.

Beavis, R., et al "Matrix-assisted laser desorption/ionization mass spectrometry of biopolymers," *Anal. Biochem.*, 1991, 63:1193-1203.

Chen, C. N., et al, "Ordered shotgun sequencing of a 135 kb Xq25 YAC containing ANT2 and four possible genes, including three confirmed by EST matches," *Nucleic Acids Research*, 1996, 24:4034-4041.

Daugherty P.S., et al., "Antibody affinity maturation using bacterial surface display," *Protein Eng* 1998, 11:825-32.

Delarue, M., et al., "An attempt to unify the structure of polymerases," *Protein Eng*, 1990, 3:461-467.

Fichant, G. A. and Quentin, Y., "A frameshift error detection algorithm for DNA sequencing projects," *Nucleic Acid Research*, 23:2900-2908, 1995.

Fu, D. J., et al., "Sequencing exons 5 to 8 of the p53 gene by MALDI-TOF mass spectrometry," *Nature Biotechnology*, 1998, 16:381-384.

(Continued)

*Primary Examiner*—Jezia Riley
(74) *Attorney, Agent, or Firm*—Squire, Sanders & Dempsey L.L.P.

(57) ABSTRACT

The present invention relates to methods for the detection of polymorphisms by substituting a base-modified nucleotide for a natural nucleotide in a polynucleotide. The base-modified nucleotide renders the polynucleotide more susceptible to cleavage at the sites of its incorporation than site consisting of natural nucleotides. The fragments obtained are then analyzed to determine the presence or absence of a polymorphism.

20 Claims, 15 Drawing Sheets

OTHER PUBLICATIONS

Giese, B., et al, "The chemistry of single-stranded 4'-DNA radicals: influence of the radical precursor o anaerobic and aerobic strand cleavage," *Chemistry & Biology*, 1995, 2 No. 6, 367-375.

Giese, B., et al, "The mechanism of anaerobic, Radical-Induced DNA strand scission," Angew. *Chem. Int. Ed. Engl.* 1993, 32:1742-43.

Gish, G., et al "DNA and RNA Sequence Determination Based on Phosphorothioate Chemistry," *Reports*, 1988 1520-1522.

Gupta and Kool, "A self-cleaving DNA nucleoside," *Chem. Commun*: 1997, pp 1425-1426.

Harayama, S., "Artificial evolution by DNA shuffling," *Trends Biotechnol.*, 1998, 16:76-82.

Hentosh, P. et al, "Ploymerase chain reaction amplification of single-stranded DNA containing a base analog, 2-Chloroadenine,". *Anal. Biochem.*, 1992, 201:277-281.

Huang, Y., "Determinants of Ribose Specifity in RNA Polymerization: Effects of $Mn^{2+}$ and Deoxynucleoide Monophosphate Incorporation into Transcripts," *Biochemistry*, 1997, 36:13718-13728.

Joyce, C. M., "Choosing the right sugar: How polymerases select a nucleotide substrate," *Proc. Natl. Acad. Sci. USA*, 1997, 94:1619-1622.

Kaczorowski, T., et al., "Assembly of 18-nucleotide primers by ligation of three hexamers: secuqncing of large genomes by primer walking," *Anal. Biochem.*, 1994, 221:127-135.

Khurshid, F., et al, "Error analysis in manual and automated DNA sequencing," *Analytical Biochemistry*, 208:138-143, 1993.

Kirpekar, F., et al, "Matrix-assisted laser desorption-ionization mass spectrometry of enzymatically synthesized RNA up to 150 kDa," *Nucleic Acids Research*, 1994, 22: No. 19 3866-3870.

Kristensen, T., et al, "An estimate of the sequencing error frequency in the DNA sequence databases," *DNA Sequencing*, 2:343-346, 1992.

Landegren, U. et al., Reading Bits of Genetic Information: Methods for Single-nucleotide Polymorphism Analysis, *Genome Research* 1998, 88:769-76.

Liu, D., et al., "Bi-stranded, multisite replication of a base pair between difluorotoluene and Adenine: confirmation by 'inverse' sequencing," *Chem. Biol.*, 4:919-929, 1997.

Lodhi, M. A., et al., "High-quality automated DNA sequencing primed with hexamer strings," *Genome Research*, 1996, 6:10-18.

Martin-Gallardo, et al., "Automated DNA sequencing and analysis of 106 kilobases from human chromosome 19q13. 3," *Nature Genetics*, 1992 1:34-39.

Marx, A., et al, "Synthesis of 4'-C-Acylated Thymidines," *Helv. Chim. Acta*, 1966, 79:1980-94.

Maxam and Gilbert, "A new method for sequencing DNA" *Proc. Nat. Acad. Sci.* USA, 74, 560-564 1977.

Moran, S., et al., "A thymidine triphosphate shape analog lacking Watson-Crick pairing ability is replicated with high sequence selectivity," *Proc. Natl. Acad. Sci. USA*, 94: 10506-10511, 1997.

Nakamaye, K. et al, "Direct sequencing of polymerase chain reaction amplified DNA fragments through the incorporation of deoxynucleoside α-thiotriphosphates," *Nucleic Acid Research*, 1988, 16:9947-9959.

Nelson, R.W., et al, "Volatilization of High Molecular Weight DNA by Pulsed Laser Ablation of Frozen Aqueous Solutions," *Science* 1989, vol. 246, 1585-1587.

Nickerson, D.A., "DNA sequence diversity in a 9.7-kb region of the human lipoprotein ilipase gene," *Nature Genetics*, 1998, 223-240.

Nordhoff, E. et al, "Comparison of IR- and UV-matrix-assisted laser desorption/ionization mass spectrometry of oligodeoxynucleotides," *Nucleic Acids Research*, 1994, 22: No. 13, 2460-2465.

Nordhoff, E. et al, "Ion stability of nucleic acids in infrared matrix-assisted laser desorption/ionization mass spectrometry," *Nucleic Acids Research*, 1993, 21:No. 15 3347-3357.

Olsen, D.B. et al, "[8] Direct sequencing of polymerase chain reaction products," *Methods of Enzymology*, vol. 218 pp 79-92, 1993.

Ono, T., et al., "2'-Floro modified nucleic acids: polymerase-directed synthesis, properties and stability to analysis by matrix-assisted laser desorption/ionization mass spectrometry," *Nucleic Acids Research*, 1997, 25: 4581-4588.

Pedersen et al., "A method for directing evolution and functional cloning of enzymes," *Proc. Natl. Acad. Sci. USA*, 1998, 95:10523-8.

Pieles, U, et al, "Matrix-assisted laser desorption ionization time-of-flight mass spectrometry: a powerful tool for the mass and sequence analysis of natural and modified oligonucleotides," *Nucleic Acids Research*, 1993, 21:No. 14 3191-3196.

Polesky et al., "Identification of residues critical for the polymerase activity of the Klenow fragment of DNA polymerase I from *Escherichia coli*,*" J. Biol. Chem.*, 1990, 265:14579-91.

Pomerantz, S.C., et al., "Determination of oligonucleotide composition from Mass spectrometrically measured molecular weight," *J. Am. Soc. Mass Spectrom.*, 1993, 4: 204-209.

Prober, et al, "A System for Rapid DNA Sequencing with Fluorescent Chain-Terminating Dideoxynucleotides," *Science* 1987, vol. 238, 336-341.

Sanger, et al., "DNA sequencing with chain-terminating inhibitors," *Proc. Nat. Acad. Sci. USA*, 74, 5463-5467 1977.

Schneider, K. and Chait, B.T., "Increased stability of nucleic acids containing 7-deaza-quanosine and 7-deaza-adenosine may enable rapid DNA sequencing by matrix-assisted laser desorption mass spectrometry," *Nucleic Acids Research*, 1995, 23: 1570-1575.

Siebenlist, et al., "Contacts between *Escherichia coli* RNA polymerase and an early promoter of phase T7," *Proc. Natl. Acad. Sci. USA*, 1980, 77:122.

Siuzdak, G. "The emergence of mass spectrometry in biochemical research," *Proc. Natl. Acad. Sci.*, 1994, 91: 11290-11297.

Sousa, et al, "A mutant T7 RNA polymerase as a DNA polymerase," *EMBO Journal* vol. 14 No. 18, pp. 4609-4621, 1995.

Stemmer, W. P. C., "Rapid evolution of a protein in vitro by DNA shuffling," *Nature*, 1994, 370:389-391.

Tabor, S., et al., "DNA sequence analysis with a modified bacteriophage T7 DNA polymerase," *Proc. Natl. Acad. Sci. USA*, 1987, 84:4767-4771.

Venter, J. C., et al., "Shotgun sequencing of the human genome," *Science*, 1998, 280:1540-1542.

Verdine, et al, "Immobilized Metal Affinity Chromatography of DNA," *Dept. of Chemistry, Harvard University*, May 29, 1996.

Verdine, et al., "Template-Directed Interference Footprinting of Cytosine Contacts in s Protein-DNA Complex: Potent Interference by 5-Aza-2'-deoxycytidine;" *Biochemistry*, 1992, 31:11265-11273.

Verdine, et al., "Template-Directed Interference Footprinting of Protein-Adenine Contacts," *JACS*, 1996, 118:6116-6120.

Verdine, et al., "Template-Directed Interference Footprinting of Protein-Guanine Contacts in DNA;" *JACS*, 1991, 113:5104-5106.

Verdine, et al., "Template-Directed Interference Footprinting of Protein-Thymine Contacts," *JACS*, 1993, 115:No. 1 373-374.

Voss, H., et al., "Automated low-redundancy large-scale DNA sequencing by primer walking," *Biotechniques*, 1993, 15:714-721.

Wang, B. H., et al "Matrix-assisted laser desorption/ionization time-of-flight mass spectrometry of chemically modified oligonucleotides," *Analytical Chemical*, 1994, 66: 1918-1924.

Wang, B. H., et al, Sequencing of modified olignucleotides using in-source fragmentation and delayed pulsed ion extraction matrix-assisted laser desorption ionization time-of-flight mass spectrometry, *Internat'l J. of Mass Spec. and Ion Process*, 1997, 169/170:331-350.

Weber, J. L. "Human whole-genome shotgun sequencing," *Genome Research*, 1997, 7:401-409.

Williams, E. R., "Tandem FTMS of Large Biomolecules," *Anal. Chem.*, 1998, 70:179A-185A.

Wu, K., et al, "Time-of-flight mass spectrometry of underivatized single-stranded DNA oligomers by matrix-assisted laser desorption," *Anal. Chem*, 1994 66, 1637-1645.

* cited by examiner

FIGURE 1

5'-AACTGGACAGCACAGACTTCACCA(G)GCACCATCAAGCTGCTGAATGAA
AATTCATATGTCCCTCGTGAG-3' [SEQ. ID. NO. 1]

3'-CTTTGACCTGTCGTGTCTGAAGTGGT(C)CGTGGTAGTTCGACGACTTACT
TTTAAGTATACAGGGAGCACTC-5' [SEQ. ID. NO. 2]

5'-CTGAAGAGAAAGTTGTCGGAGAAACTGGACAGCACAGACTTCACCA(G)G
CACCATCAAGCTGCTGAA-3' [SEQ. ID. NO. 3]

3'-ACAACTCTTTCAACAGCCTCTTTGACCTGTCGTGTCTGAAGTGGT(C)CGT
GGTAGTTCGACGACTT-5' [SEQ ID. NO. 4]

5'-TGAAGAGAAAGTTGTCGGAGAAACTGGACAGCACAGACTTCACA(G)GCA
CCATCAAGCTGCTGAATG-3' [SEQ. ID. NO. 5]

3'-ACAACTCTTTCAACAGCCTCTTTGACCTGTCGTGTCTGAAGTGGT(C)CGT
GGTAGTTCGACGACTTAC-5' [SEQ. ID.NO. 6]

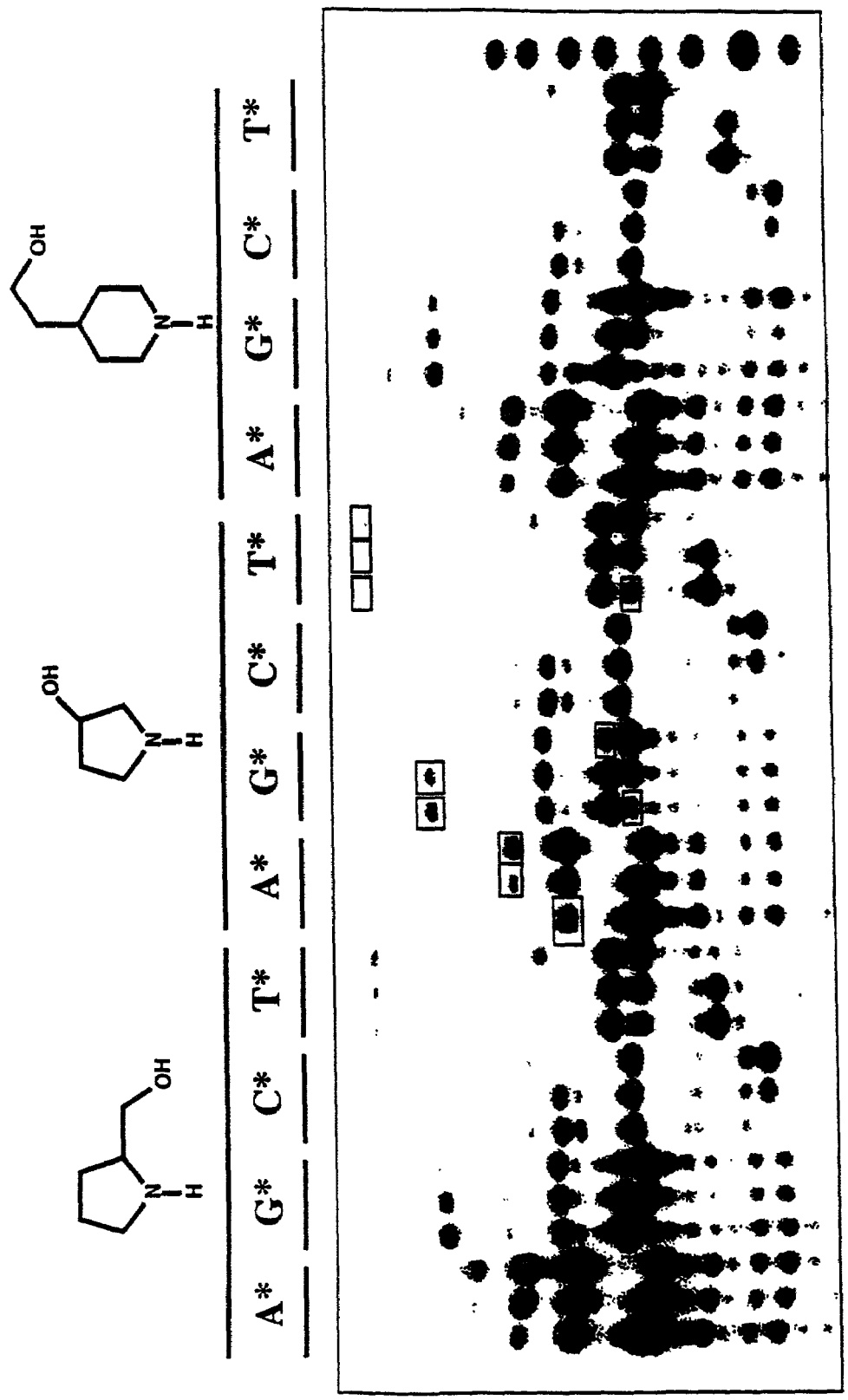

5'-<u>GAAACTGGACAGCACAGACTT</u>CACCAGCACCATCAAGCTGCTGAATGAA
3'-CTTTGACCTGTCGTGTCTGAAGTGGTCGTGGTAGTTCGACGACTTACTTT

```
    A     G
       vs
    T     C
```

AATTCATATGTCCCTCGTGAGGCTGGATCTCAA-3' [SEQ. ID. NO. 7]
TAAGTATACAG<u>GGAGCACTCCGACCTAGAGTT</u>-5' [SEQ. ID. NO. 8]

| | |
|---|---|
| AmpliTaq Gold | 0.1 unit.ml |
| DA*TP (modified A) | 0.2 mM |
| dCTP, dGTP, dTTP | 0.2 mM |

| | LENGTH | MW | ΔMW |
|---|---|---|---|
| 5'-<u>GAAACTGGACAGCAC AGACTTCA</u>CC [SEQ. ID. NO. 9] | 25nt | 8057 | |
| or | | | 948 Da |
| 5'-<u>GAAACTGGACAGCAC AGACTTCA</u>CCGGC [SEQ. ID. NO. 10] | 28nt | 9005 | |
| <u>GGGAGCACTCCGACC TAGAGTT</u>-5' [SEQ. ID. NO. 11] | 22nt | 7189 | |
| CCTGTCGTGTCTG-5' [SEQ. ID. NO. 12] | 13nt | 4441 | |
| GTGGTCGTGGT-5' [SEQ. ID. NO. 13] | 11nt | 3927 | |
| or | | | 15 Da |
| GTGGCCGTGGT-5' [SEQ. ID. NO. 14] | 11nt | 3912 | |
| 5'-TGTCCCTCGTG [SEQ. ID. NO. 15] | 11nt | 3807 | |

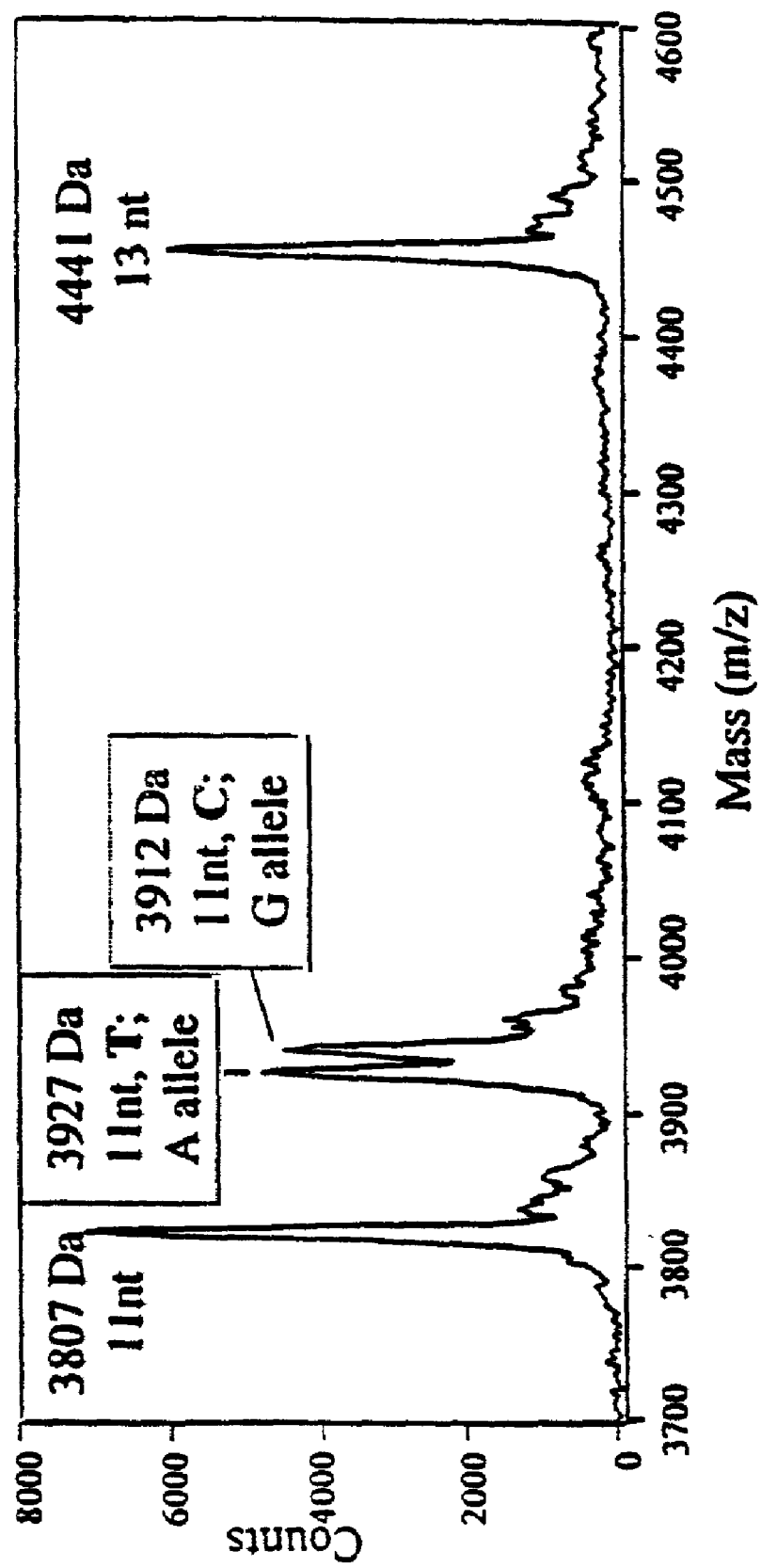

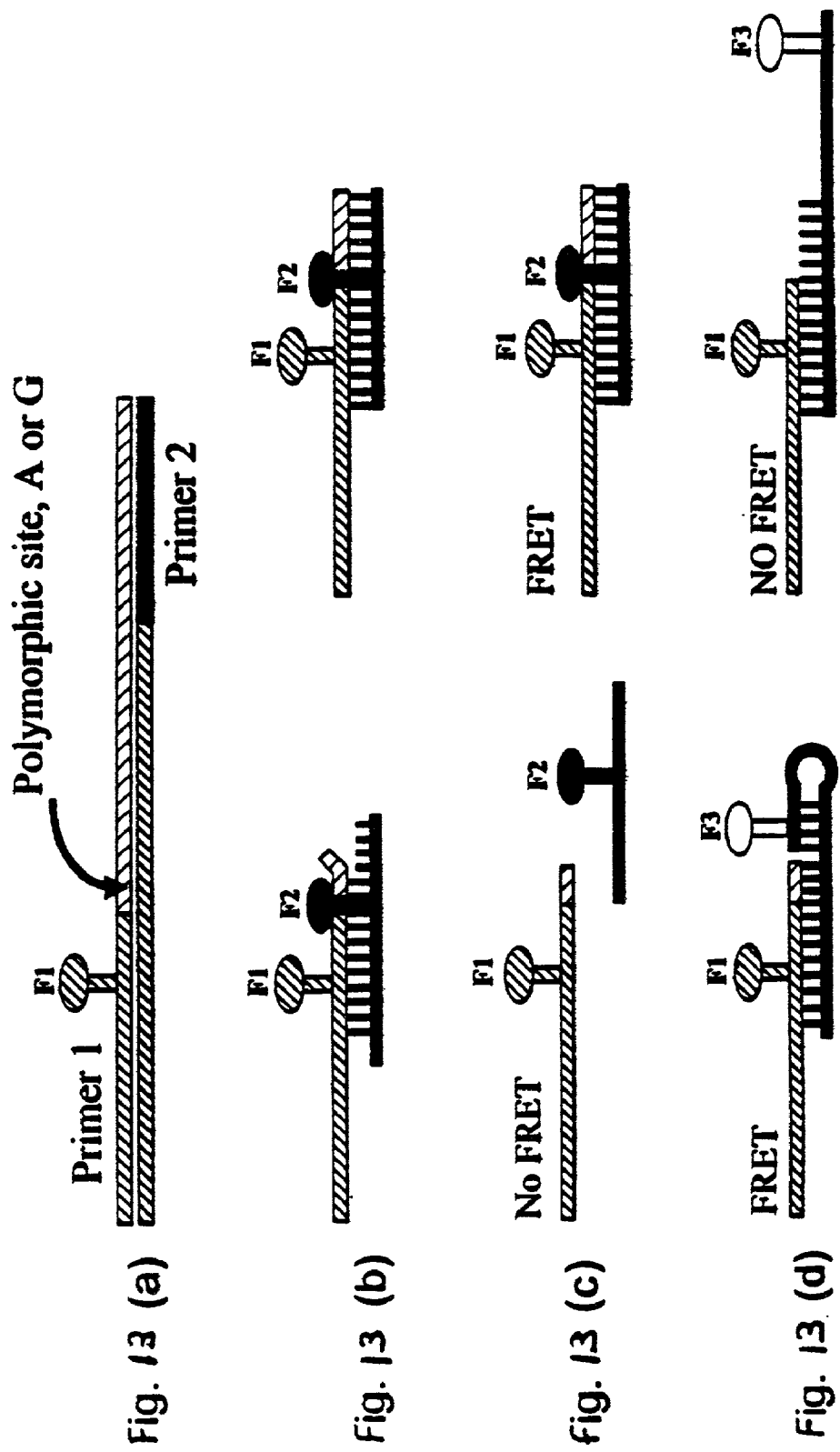

BASE-MODIFIED NUCLEOTIDES AND THEIR USE FOR POLYMORPHISM DETECTION

RELATED APPLICATIONS

This application is a continuation-in-part of U.S. Ser. No. 09/394,467 to Stanton, Wolfe, and Verdine, filed Sep. 10, 1999, now U.S. Pat. No. 6,566,059, entitled "A METHOD FOR ANALYZING POLYNUCLEOTIDES." Ser. No. 09/394,467 in turn claims the benefit of U.S. Provisional Patent Application Ser. No. 60/102,724, filed Oct. 1, 1998, also entitled "A METHOD FOR ANALYZING POLYNUCLEOTIDES." Both are incorporated by reference in their entireties, including drawings and tables, as if fully set forth herein.

FIELD OF THE INVENTION

The present invention relates generally to organic chemistry, analytical chemistry, biochemistry, molecular biology, genetics, diagnostics and medicine. In particular, it relates to base-modified nucleotides and methods for their use for the detection polymorphisms (SNPs).

BACKGROUND OF THE INVENTION

The following is offered as background information only and is not intended nor admitted to be prior art to the present invention.

The ability to detect DNA sequence variances in an organism's genome has become an important tool in the diagnosis of diseases and disorders and in the prediction of response to potential therapeutic regimes. It is becoming increasingly possible, using early variance detection, to diagnose and treat, even prevent, a disorder before it has physically manifested itself. Furthermore, variance detection can be a valuable research tool in that it may lead to the discovery of genetic bases for disorders the cause of which were hitherto unknown or thought to be other than genetic.

It is estimated that sequence variations in human DNA occur with a frequency of about 1 in 100 nucleotides when 50 to 100 individuals are compared. Nickerson, D. A., *Nature Genetics,* 1998, 223–240. This translates to as many as 30 million variances in the human genome. However, very few of these variances have any effect on the physical well-being of humans. Detecting these 30 million variances and then determining which of them are relevant to human health is clearly a formidable task.

Once the DNA sequence of a DNA segment; e.g., a gene, a cDNA or, on a larger scale, a chromosome or an entire genome, has been determined, the existence of sequence variances in that DNA segment among members of the same species can be explored. Complete DNA sequencing is the definitive procedure for accomplishing this task. However, current DNA sequencing technology is costly, time consuming and, in order to assure accuracy, highly redundant. Most sequencing projects require a 5- to 10-fold coverage of each nucleotide to reach an acceptable error rate of 1 in 2,000 to 1 in 10,000 bases. In addition, DNA sequencing is an inefficient way to detect variances. A variance between two copies of a gene, for example when two chromosomes are being compared, may occur as infrequently as one in 1,000 or more bases. Thus, only a small segment of the gene is of interest. If full sequencing is employed, a tremendous number of nucleotides have to be sequenced to arrive at the desired information contained in that segment. For example, to compare ten versions of a 3,000 nucleotide DNA sequence for the purpose of detecting four variances among them, even if only 2-fold redundancy is employed (each strand of the double-stranded 3,000 nucleotide DNA segment from each individual is sequenced once), 60,000 nucleotides would have to be sequenced (10×3,000×2). In addition, sequencing problems are often encountered that can require additional runs with new primers. Thus, as many as 100,000 nucleotides might have to be sequenced to determine four variances.

What is needed is a rapid, inexpensive, yet accurate method to identify variances such as SNPs among related polynucleotides. The present invention provides such a method and materials for its implementation.

SUMMARY OF THE INVENTION

Thus, in one aspect, the present invention comprises a method for detecting a polymorphism in a polynucleotide. The method comprises, first, providing a target polynucleotide. A natural nucleotide is replaced at greater than 90% of its points of occurrence in the target polynucleotide, provided the points of occurrence are not in a primer sequence, with a base-modified nucleotide to give a modified target polynucleotide. The modified target polynucleotide is contacted with a reagent or combination of reagents that cleaves it at greater than 90% of the base-modified nucleotides to give a set of fragments. The set of fragments is then analyzed to detect a polymorphism. In this method the base-modified nucleotide is selected from the group consisting of:

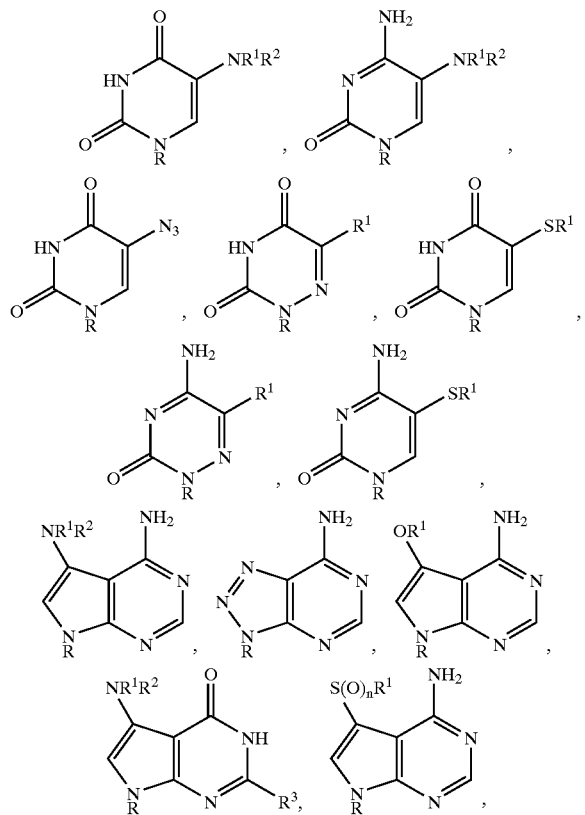

-continued

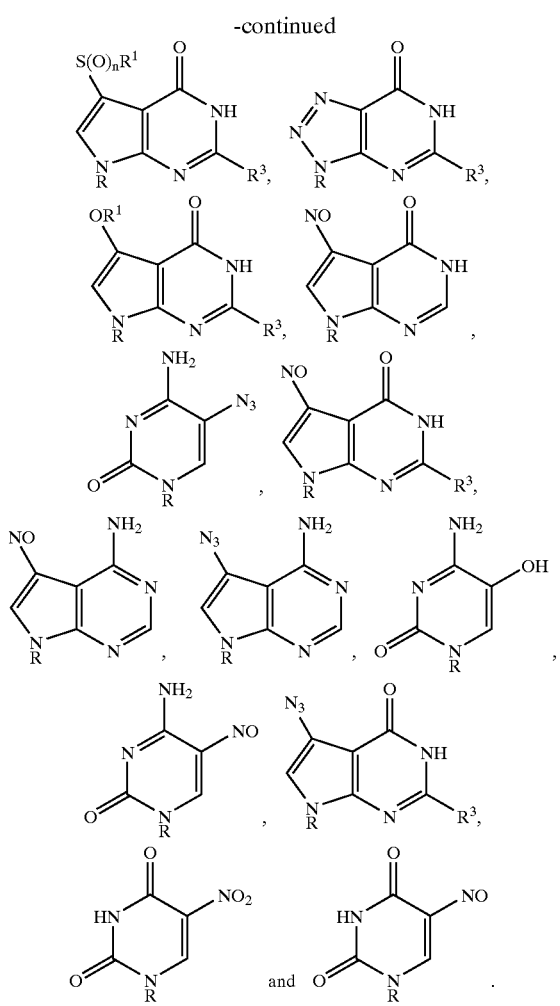

R is a ribose or a deoxyribose moiety of a polynucleotide. $R^1$ and $R^2$ are independently selected from the group consisting of hydrogen, alkyl, cycloalkyl, alkenyl, alkynyl, aryl, aralkyl and alkaryl, wherein, if $R^1$ or $R^2$ contains two or more contiguous methylene (—CH$_2$—) groups, any two such methylene groups may have interjected between them a group selected from the group consisting of —O—, —C(O)NH—, —C(O)NHC(O)—, —NH—, —C(S)NH—, —CO—, —CS—, —S— and (—CF$_2$—)$_m$. Furthermore, m is 1–10. $R^3$ is hydrogen or —NH$_2$. And, finally, n is 0, 1 or 2.

In a further aspect of this invention, the base-modified nucleotide is selected from the group consisting of:

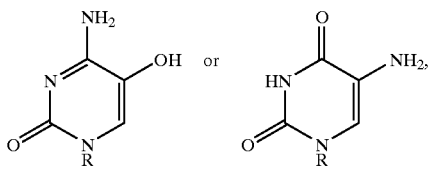

R is a ribose or deoxyribose moiety of an oligonucleotide.

In an aspect of this invention, contacting the base modified polynucleotide with a reagent or reagents comprises contacting it with a chemical base.

In an aspect of this invention the chemical base comprises a secondary amine having a boiling point above 100° C. at atmospheric pressure.

In an aspect of this invention, the secondary amine has a boiling point above 150° C. at atmospheric pressure. Most preferably, the secondary amine has a boiling point greater than 200° C. at atmospheric pressure.

In an aspect of this invention, the secondary amine is selected from the group consisting of 3-pyrrolidinol, 2-pyrrolidinemethanol, 3-pyrrolidinemethanol, 4-hydroxypiperidine and 4-piperidineethanol.

In an aspect of this invention, analysis of the fragments comprises gel electrophoresis.

In as aspect of this invention, analysis of the fragments comprises mass spectrometry.

In an aspect of this invention, mass spectrometry comprises MALDI mass spectrometry.

In an aspect of this invention, mass spectrometry comprises ESI mass spectrometry.

In an aspect of this invention, analyzing the fragments comprises comparing the masses of the fragments with masses of fragments predicted if the polymorphism is present or with masses of fragments predicted if the polymorphism is not present.

An aspect of this invention relates to a method for detecting a polymorphism in a polynucleotide, comprising replacing a natural nucleotide at greater than 90% of its points of occurrence in the target polynucleotide, provided the points of occurrence are not in a primer sequence, with a modified nucleotide to give a modified target polynucleotide. The modified target polynucleotide is contacted with a secondary amine having a boiling point greater than 100° C. at atmospheric pressure, at a temperature that results in cleavage of the modified polynucleotide at greater than 90% of the modified nucleotides, to give a set of fragments. The fragments are then analyzed to detect a polymorphism.

In an aspect of this invention, the above secondary amine has a boiling point greater than 150° C. at atmospheric pressure.

In an aspect of this invention, the secondary amine has a boiling point greater than 200° C. at atmospheric pressure.

In an aspect of this invention, the secondary amine is selected from the group consisting of 3-pyrrolidinol, 2-pyrrolidinemethanol, 3-pyrrolidinemethanol, 4-hydroxypiperidine and 4-piperidineethanol.

In an aspect of this invention, the polynucleotide is contacted with a chemical oxidant prior to contact with the secondary amine. The chemical oxidant comprises potassium permanganate in an presently preferred aspect of this invention.

In any of the above methods, the percentage replacement of a natural nucleotide with a modified nucleotide, the percentage cleavage of a modified polynucleotide or both the percentage replacement and the percentage cleavage is greater than 95% in an aspect of this invention.

In any of the above methods, the percentage replacement of a natural nucleotide with a modified nucleotide, the percentage cleavage of a modified polynucleotide or both the percentage replacement and the percentage cleavage is greater than 99% in an aspect of this invention.

DETAILED DESCRIPTION OF THE INVENTION

Brief Description of the Tables

Table 1 shows the molecular weights of the four DNA nucleotide monophosphates and the mass difference between each pair of nucleotides.

Table 2 shows the masses of all possible 2mers, 3mers, 4mers and 5mers of the DNA nucleotides in Table 1.

Table 3 shows the masses of all possible 2mers, 3mers, 4mers, 5mers, 6mers and 7mers that would be produced by cleavage at one of the four nucleotides and the mass differences between neighboring oligonucleotides.

Table 4 shows the 8 sets of isobaric (masses within 0.01% of each other) oligonucleotides that are found among all oligonucleotides up to 30mers.

Table 5 shows the mass changes that will occur for all possible point mutations (replacement of one nucleotide by another) and the theoretical maximum size of a polynucleotide in which a point mutation should be detectable by mass spectrometry using mass spectrometers of varying resolving powers.

Table 6 shows the expected molecular weights for the commercial RFC primer, RFC mut primer and RFC mut primer with a G deletion.

BRIEF DESCRIPTION OF THE FIGURES

FIG. 1 shows the sequence of oligonucleotides used to examine the cleaving ability of various secondary amines [SEQ. IDs. 1–6]

FIG. 2 shows the result of cleavage of the oligonucleotides depicted in FIG. 1 using 2-pyrrolidinemethanol, 3-pyrrolidinol and 4-piperidineethanol.

FIGS. 7–13 show various aspects of genotyping using the methods of this invention.

FIG. 7(b) shows the fragments [SEQ. IDs 9–15] expected from cleavage at the modified nucleotide of 7(a).

FIG. 8 illustrates genotyping by detection by mass differences obtained from the amplification and cleavage of the variant forms of transferrin receptor. Only the fragments that illustrate the length and mass differences among the fragments of the same (invariant) and different (variant) alleles are shown.

FIG. 9 shows the mass spectra of the three possible genotypes of the transferrin receptor gene used in FIG. 8.

FIG. 10 is another illustration of genotyping by mass spectrometry. The spectrum is a MALDI-TOF analysis of a chemically cleaved DNA fragment. The boxed areas are regions that contain fragments with polymorphism.

FIG. 11 illustrates genotyping by chemical cleavage followed by electrophoresis. The capillary electrophoresis analysis of a chemically cleaved polymorphic DNA fragment is depicted.

FIG. 12 shows the denaturing 20% PAGE analysis of the chemically cleaved amplicon of FIG. 11.

FIG. 13 (a)–(d) illustrate genotyping by fluorescence resonance energy transfer (FRET): (A) amplify template using one modified, cleavable nucleotide (DA*TP). Primer 1 is modified with a fluor, F1; (B) after cleavage a probe modified with a second fluor, F2, and complementary to primer 1 is added; (C) at elevated temperature, the allele shortened by cleavage is not bound to the probe (and, therefore, no FRET is produced) while the uncleaved allele remains bound giving a FRET. (D) shows a means for positive detection of the short fragment by modifying the probe to contain a hairpin and an additional fluor, F3. The hairpin will open only after binding with the longer, uncleaved fragment resulting in a difference in FRET production.

DEFINITIONS

Figure 3:
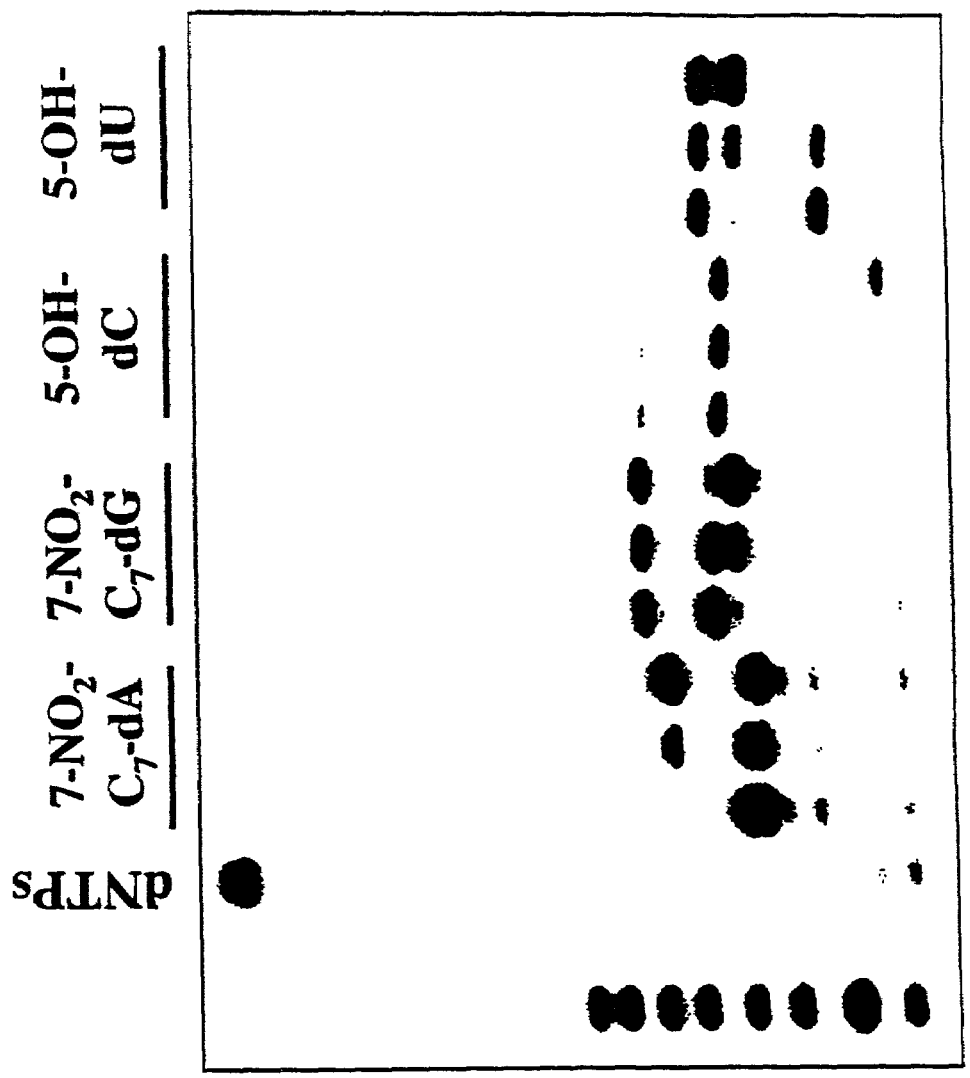
FIG. 3 shows the result of cleavage of the oligonucleotides depicted in FIG. 1 using 3-pyrrolidinol at a higher temperature.

As used herein, the term "detecting" refers to the determination of the presence or absence of a variance, in particular one or more single nucleotide polymorphisms (SNPs) in the nucleotide sequence of a polynucleotide when compared to a related polynucleotide.

As used herein, a "reagent" refers to a chemical entity or physical force that causes the cleavage of a modified polynucleotide at point(s) where a modified nucleotide is substituted for a natural nucleotide. Such reagents include, without limitation, a chemical or combination of chemicals, normal or coherent (laser) visible or uv light, heat, high energy ion bombardment and irradiation. A "combination of reagents" refers two or more reagents, which can be used simultaneously or sequentially. By simultaneously is meant that the two or more reagents are together placed in contact with a modified polynucleotide to be cleaved although it is understood that they may in fact react with the polynucleotide one at a time. By sequentially is meant that the polynucleotide is contacted with one reagent and then, when that reaction is complete, a second reagent is added, and so on. For instance, as described in the Examples section of this disclosure, it may be necessary or desirable to contact a modified polynucleotide of this invention with an oxidizing agent prior to contacting it with a chemical base to effect cleavage.

As used herein, the terms "cleaving," "cleaved" and "cleavage" all relate to the scission of a polynucleotide chain at substantially each point of occurrence in the polynucleotide chain of a base-modified nucleotide of this invention. The polynucleotide chain may be single-stranded or double-stranded. When primers are used to amplify or otherwise replicate a template to obtain a version of the polyhucleotide with a base-modified nucleotide incorporated in place of each corresponding natural nucleotide, i.e., to create a modified polynucleotide, it is to be understood that the primer does not take part in the replacement or cleavage reaction. That is, no natural nucleotide in the primer is replaced with a modified nucleotide and the primer is not cleaved.

As used herein, a "related" polynucleotide is a polynucleotide obtained from a source genetically similar to that from which another polynucleotide is obtained such that the nucleotide sequences of the two polynucleotides would be expected to be exactly the same in the absence of a variance. As used herein, polynucleotides that have overlapping sequences of 35 nucleotides or more that, in the absence of a variance, would be exactly the same are considered "related" polynucleotides.

As used herein, a "variance" is a difference in nucleotide sequence among related polynucleotides. Except as otherwise stated, the term "mutation" and is used interchangeably with "variance" herein. A variance may involve the addition or deletion of a nucleotide from the sequence of one polynucleotide compared to the sequence of a related polynucleotide. Or, it may be the substitution of one nucleotide for another. As used herein, the term "variance" in the singular is understood to include multiple variances; i.e., two or more nucleotide additions, deletions and/or substitutions in the same polynucleotide. A particular type of variance is the "polymorphism" or "single nucleotide polymorphism," which, as the name suggests, is a variance consisting of a single substitution of one nucleotide for another.

Thus, as used herein, a "single nucleotide polymorphism" or "SNP" refers to a polynucleotide that differs from another polynucleotide at a particular locus by virtue of a single nucleotide exchange. A polynucleotide may, of course, contain numerous SNPs; however, each must occur at a different locus and consist of a single nucleotide exchange. For example, exchanging one A for one C, G or T at a particular locus in the sequence of a polynucleotide constitutes a SNP. When referring to SNPs, the polynucleotide is most often genetic DNA. As such, to qualify at a SNP, the polymorphism must occur at a frequency greater than 1% in a given population. SNPs can occur in coding and non-coding regions of the gene. Those in coding regions are of primary interest because it is they that cause changes in the phenotype, i.e., a detectable physical difference, of an individual compared to the general population. Detectable physical differences include, without limitation, a difference in susceptibility to a particular disease or disorder or a difference in response to a therapeutic regime used to treat or prevent a disease or disorder.

As used herein a "target polynucleotide" simply refers to a polynucleotide that is suspected to contain a variance and therefore is being subjected to the method of this invention to determine whether or not it does.

As used herein, a "reference polynucleotide" refers to a polynucleotide that is related to a test polynucleotide but is known to either contain or not contain the subject polymorphism.

As used herein the phrase "suspected of containing a variance" refers to a test polynucleotide in which a difference in the nucleotide sequence at a particular locus is known generally to occur in some individuals compared to the general population but it is unknown whether that difference exists in the test polynucleotide. When the test and related nucleotides are genetic DNA, the difference in their sequences consist of the exchange of a single nucleotide at a given position in the sequence and the frequency of such exchange in the population is 1% or greater, the test polynucleotide may be characterized as being "suspected of containing a polymorphism (or SNP)".

As used herein, "amplifying a segment" refers to the process of producing multiple copies of a segment of a double stranded polynucleotide by hybridizing natural nucleotide primers 3' to the segment on each strand and then treating the strands with one or more polymerases to extend both strands. As a result of using two strands and two primers, the process becomes logarithmic. The most common procedure for accomplishing amplification is the polymerase chain reaction or PCR, which is well known to those skilled in the art. The end result of amplification is the production of a sufficient amount of the segment to permit relatively facile manipulation. Manipulation refers to both physical and chemical manipulation, that is, the ability to move bulk quantities of the segment around and to conduct chemical reactions with the segment that result in detectable products.

As used herein, "primer extension" refers to the reproduction of the sequence of a segment of a polynucleotide by hybridization of a natural nucleotide primer to the polynucleotide 3' of the segment followed by treatment with a polymerase and four nucleotides, one or more of which may be a modified nucleotide, to extend the primer and create a copy of the segment.

As used herein a "segment" of a polynucleotide refers to a portion of the complete nucleotide sequence of the polynucleotide.

As used herein a "modified segment" refers to a segment in which one or more natural nucleotides have been replaced with one or more base-modified nucleotides.

As used herein, a "modified, labeled segment" refers to a modified segment that also contains an entity that is readily detectable, visually or by instrumental means.

As used herein, the phrase "encompassing the suspected polymorphism" means that the nucleotide or nucleotides that constitute a variance are included in the sequence of a selected segment of the polynucleotide.

By "homozygous" is meant that the two alleles of a diploid cell or organism have exactly the same nucleotide sequence.

By "heterozygous" is meant that the two alleles of a diploid cell or organism have a difference in their nucleotide sequence at a particular locus. In most cases, the difference is a SNP.

A "sequence" or "nucleotide sequence" refers to the order of nucleotide residues in a nucleic acid.

A "nucleoside" refers to a base linked to a sugar. The base may be adenine (A), guanine (G) (or its substitute, inosine (I)), cytosine (C), or thymine (T) (or its substitute, uracil (U)). The sugar may be ribose (the sugar of a natural nucleotide in RNA) or 2-deoxyribose (the sugar of a natural nucleotide in DNA).

A "nucleoside triphosphate" refers to a nucleoside linked to a triphosphate group (O$^-$—P(=O)(O$^-$)—O—P(=O)(O$^-$)—O—P(=O)(O$^-$)—O-nucleoside). The triphosphate group has four formal negative charges that require counterions, i.e., positively charged ions. Any positively charged ion can be used, e.g., without limitation, Na$^+$, K$^+$, NH$_4^+$, Mg$^{2+}$, Ca$^{2+}$, etc. Mg$^{2+}$ is one of the most commonly used counter-ions. It is accepted convention in the art to omit the counter-ion, which is understood to be present, when displaying nucleoside triphosphates; the convention is followed in this application.

As used herein, unless expressly noted otherwise, the term "nucleoside triphosphate" or reference to any specific nucleoside triphosphate; e.g., adenosine triphosphate, guanosine triphosphate or cytidine triphosphate, refers to a triphosphate comprising either a ribonucleoside or a 2'-deoxyribonucleoside.

A "nucleotide" refers to a nucleoside linked to a single phosphate group.

A "natural nucleotide" refers to an A, C, G or U nucleotide when referring to RNA and to dA, dC, dG and dT (the "d" referring to the fact that the sugar is a deoxyribose) when referring to DNA. A natural nucleotide also refers to a nucleotide which may have a different structure from the above, but which is naturally incorporated into a polynucleotide sequence by the organism which is the source of the polynucleotide.

As used herein, a "modified nucleotide" refers to a nucleotide that meets two criteria. First, a modified nucleotide is a "non-natural" nucleotide. In one aspect, a "non-natural" nucleotide may be a natural nucleotide that is placed in non-natural surroundings. For example, in a polynucleotide that is naturally composed of deoxyribonucleotides, e.g., DNA, a ribonucleotide would constitute a "non-natural" nucleotide. Similarly, in a polynucleotide that is naturally composed of ribonucleotides, i.e., RNA, a deoxyribonucleotide would constitute a non-natural nucleotide. A "non-natural" nucleotide also refers to a natural nucleotide that has been chemically altered. For example, without limitation, one or more substituent groups may be added to the base, sugar or phosphate moieties of the nucleotide. On the other hand, one or more substituents may be deleted from the base, sugar or phosphate moiety. Or, one or more atoms or substituents may be substituted for one or more others in the nucleotide. A "modified" nucleotide may also be a molecule that resembles a natural nucleotide little, if at all, but is nevertheless capable of being incorporated by a polymerase into a polynucleotide in place of a natural nucleotide. In particular with respect to the present invention, the modified nucleotide is a base-modified nucleotide. By "base-modified nucleotide" is meant a nucleotide in which the normal heterocyclic nitrogen base, adendine, guanine, cytosine, thymine or uracil, is chemically modified by the addition, delection and/or substitution of one or more substituents or atoms for that in the normal base.

The second requirement for a "modified" nucleotide, as the term is used herein, is that it alters the cleavage properties of the polynucleotide into which it is incorporated. For example, without limitation, incorporation of a ribonucleotide into a polynucleotide composed predominantly of deoxyribonucleotides imparts a susceptibility to alkaline cleavage at the sites of incorporation that does not otherwise exist. This second criterion of a "modified" nucleotide may be met by substitution of one non-natural nucleotide for a natural nucleotide (e.g., the substitution of a ribonucleotide for a deoxyribonucleotide described above). It may also be met by substitution of two non-natural nucleotides that do not individually alter the cleavage properties of a polynucleotide, for their natural counterparts. When in a particular spatial relationship to one another in a polynucleotide into which they have been incorporated, enhanced cleavage of the polynucleotide will occur at the site of incorporation (referred to as "dinucleotide cleavage").

As used herein, "having different cleavage characteristics" refers to two or more modified nucleotides that, when incorporated into a polynucleotide, can be selectively cleaved in each other's presence by using different reagents and/or reaction conditions.

As used herein, a "label" or "tag" refers to a molecule that can be attached to another molecule, such as, without limitation, a polynucleotide or a segment thereof, to provide a means by which the other molecule can be readily detected. In the case of polynucleotides or segments thereof, the attachment can be accomplished by, for example, covalent bonding or hybridization. Two common types of tags that are useful in the methods of this invention are fluorescence (or fluorescent) tags and radiolabels or radioactive tags. When excited by light at a selected wavelength, a fluorescence tag emits light at a different wavelength that can be detected visually or instrumentally (e.g., a UV spectrophotometer). The fluorescing entity is sometimes referred to as a "fluorophore." A radiolabel or radioactive tag emits radioactive particles detectable with an instrument such as, without limitation, a scintillation counter.

A "mass-modified" nucleotide is a nucleotide in which an atom or chemical group has been added, deleted or substituted for another group solely for the purpose of changing the mass of the molecule. That is, it does not alter the cleavage properties of a polynucleotide into which it is incorporated.

A "polynucleotide" refers to a linear chain of 30 or more nucleoside 5'-monophosphate residues linked by phosphodiester bonds between the 3' hydroxyl group of one sugar and the 5' hydroxyl group of the next.

A "modified polynucleotide" refers to a polynucleotide in which a natural nucleotide has been substantially completely replaced at each point of its occurrence with a modified nucleotide. It may also refer to the substantially complete replacement of two, three or four natural nucleotides with two, three or four modified nucleotides where each of the modified nucleotides alters the cleavage properties of the resulting modified polynucleotide differently such that cleavage can be carried out independently for each modified nucleotide.

As used herein, to "alter the cleavage properties" of a polynucleotide means to render the polynucleotide more or less susceptible to cleavage at the point of incorporation of a modified nucleotide than a related polynucleotide having a natural nucleotide or a different non-natural nucleotide at the same locus. It is presently preferred to "alter the cleavage properties" by rendering a polynucleotide more susceptible to cleavage at the sites of incorporation of modified nucleotides than at other sites in the molecule. As used herein, the use of the singular when referring to nucleotide substitution is to be construed as including substitution at substantially each point of occurrence of the natural nucleotide unless expressly noted to be otherwise.

As used herein, a "template" refers to a polynucleotide strand, which a polymerase uses as a means of recognizing which nucleotide it should next incorporate into a growing strand to duplicate a polynucleotide. If the polynucleotide is DNA, it may be single-stranded or double-stranded. When employing the polymerase chain reaction (PCR) to amplify a template in the method of this invention, it is understood that, although the initial copies will be modified by incorporation of modified nucleotides, the copies themselves still serve as templates from which a polymerase is able to synthesize additional modified copies.

As used herein, a "primer" refers to an oligonucleotide formed from natural nucleotides, the sequence of which is complementary to a segment of a template to be replicated. A polymerase uses the primer as the starting point for the replication process. By "complementary" is meant that the nucleotide sequence of a primer is such that the primer can stably hybridize to the template by virtue of the formation of hydrogen bonded base-pairs over a length of at least ten consecutive bases. In the methods of this invention, a primer is never modified by incorporation of a modified nucleotide nor is it ever cleaved by the reagent or reagents used to cleave its extension product.

As used herein, a "polymerase" refers, without limitation, to DNA or RNA polymerases, mutant versions thereof and to reverse transcriptases. DNA or RNA polymerases can be mutagenized by, without limitation, nucleotide addition, nucleotide deletion, one or more point mutations, "DNA shuffling" or joining portions of different polymerases to make chimeric polymerases. Combinations of these mutagenizing techniques may also be used. A polymerase catalyzes the assembly of nucleotides to form polynucleotides. Polymerases may be used either to extend a primer once or repetitively. Repetitive extension is sometimes referred to as amplification. Amplification may be accomplished by, without limitation, PCR, NASBR, SDA, 3SR, TSA and rolling circle replication. In the methods of this invention, one or more polymerases and one or more extension or amplification techniques may be used to replicate a particular polynucleotide.

"Electrophoresis" refers to a technique for separating nucleotide fragments by size using a gel matrix across which an electrical potential has been generated. Forms of electrophoresis include, without limitation, slab gel electrophoresis and capillary electrophoresis.

"Mass spectrometry" refers to a technique for analysis of a chemical compound by examination of the masses of the fragments obtained when the compound is subjected to an ionizing potential. Forms of mass spectrometry include, without limitation, matrix assisted laser desorption ionization (MALDI) and electrospray ionization (ESI), optionally employing such features as time-of-flight, quadrupole or Fourier transform detection. While the use of mass spectrometry constitutes a preferred embodiment of this invention, other instrumental techniques may become available for the determination of the mass or the comparison of masses of oligonucleotides and polynucleotides. Any such instrumental procedure is within the scope of this invention.

"FRET" refers to fluorescence resonance energy transfer, a distance dependent interaction between the electronic excited states of two dye molecules in which energy is transferred from one dye (the donor) to another dye (the acceptor) without emission of a photon. To employ FRET in the present invention, the dye molecules are located on opposite sides of a cleavable modified nucleotide. Cleavage, with or without secondary structure formation, alters the proximity of the dyes to one another resulting in predictable changes in their fluorescence output.

FRET can result in quenching, differential light emission or depolarization. Quenching occurs when the donor absorbs light at its excitation wavelength and then, instead of emitting light at its emission wavelength, transfers some or all of its energy to the acceptor, which is not a fluorescing species. If the acceptor is a fluorescing species, upon absorbing light from the donor it emits light at its own characteristic wavelength, which is different from that of the donor. Quantitative differences in the emissions of the donor and acceptor can be used to deduce information about the molecules to which they are attached. Fluorescent depolarization can be used when the donor and acceptor are the same molecule. A donor molecule is excited with plane polarized light. If no energy is transferred to the other molecule, the light emitted by the donor will remain polarized. If, on the other hand, energy is transferred to the acceptor, which then fluoresces, the emitted light will be depolarized.

As used herein, a "chemical oxidant" refers to a reagent capable of increasing the oxidation state of a group on a molecule. For instance, without limitation, a hydroxyl group (—OH) can be oxidized to an aldehyde, ketone or acid. Some examples of chemical oxidants are, without limitation, potassium permanganate, t-butyl hypochlorite, m-chloroperbenzoic acid, hydrogen peroxide, sodium hypochlorite, ozone, peracetic acid, potassium persulfate, and sodium hypobromite.

As used herein, a "chemical base" refers to a chemical compound that, in aqueous medium, has a pK greater than 7.0. A chemical base may be inorganic or organic. Examples of inorganic chemical bases are, without limitation, alkali (sodium, potassium, lithium) and alkaline earth (calcium, magnesium, barium) hydroxides, carbonates, bicarbonates, phosphates and the like. Ammonium hydroxide is another inorganic chemical base. Nitrogen-containing organic compounds such as pyridine, aniline, quinoline, morpholine, piperidine and pyrrole are also chemical bases. Nitrogen-containing chemical bases may be primary (the nitrogen carries two hydrogen atoms and one other substituent, secondary (the nitrogen has one hydrogen and two other substituents attached) or tertiary (nitrogen carries no hydrogen atoms and three other substituents). Chemical bases may be used as aqueous solutions, which may be mild (usually due to dilution) or strong (concentrated solutions). A chemical base also refers to a strong non-aqueous organic base; examples include, without limitation, sodium methoxide, sodium ethoxide and potassium t-butoxide.

Secondary amines are presently preferred chemical bases for use in the cleavage of modified nucleotides. Secondary amines useful in the methods of this invention include, without limitation, pyrrolidine, piperidine, 3-pyrrolidinol, 2-pyrrolidinemethanol, 3-pyrrolidinemethanol, 4-piperidineethanol, hexamethyleneimine, heptamethyleneimine, diethylamine, diproylamine, dibutylamine, proline, morpholine, piperizine, picolinic acid, piperazine-2-carboxylic acid, 4-piperidineethanol and isopecotic acid. A secondary amine useful in the methods herein may also be polymer bound, for example without limitation, piperidine-4-carboxylic acid polymine resin (polystyrene).

As used herein, the term "acid" refers to a substance that dissociates in water to produce one or more hydrogen ions. An acid may be inorganic or organic. It may be a strong acid, which generally infers highly concentrated, or mild, which generally infers dilute. It is, of course, understood that acids inherently have different strengths; e.g., sulfuric acid is much stronger than acetic acid. The proper choice of acid will be apparent to those skilled in the art from the disclosures herein. Preferably, the acids used in the methods of this invention are mild. Examples of mild inorganic acids are, without limitation, dilute hydrochloric acid, dilute sulfuric acid, dilute nitric acid, phosphoric acid and boric acid. Examples, without limitation, of mild organic acids are formic acid, acetic acid, benzoic acid, p-toluenesulfonic acid, trifluoracetic acid, naphthoic acid, uric acid and phenol.

An "alkyl" group as used herein refers to a 1 to 20 carbon atom straight or branched chain hydrocarbon. Preferably the group consists of a 1 to 10 carbon atom chain; most preferably, it is a 1 to 4 carbon atom chain. As used herein "1 to 20," etc. carbon atoms means 1 or 2 or 3 or 4, etc. up to 20 carbon atoms in the chain.

An "alkenyl" group refers to an alkyl group, as defined herein, consisting of at least two carbon atoms and at least one carbon—carbon double bond. An "alkynyl" group refers to an alkyl group, as defined herein, consisting of at least two carbon atoms and at least one carbon—carbon triple bond.

A "cycloalkyl" group refers to a 3 to 8 member all-carbon monocyclic ring, an all-carbon 5-member/6-member or 6-member/6-member fused bicyclic ring or a multicyclic fused ring (a "fused" ring system means that each ring in the system shares an adjacent pair of carbon atoms with each other ring in the system) group wherein one or more of the rings may contain one or more double bonds but none of the rings has a completely conjugated pi-electron system. Examples, without limitation, of cycloalkyl groups are cyclopropane, cyclobutane, cyclopentane, cyclopentene, cyclohexane, cyclohexadiene, adamantane, cycloheptane and, cycloheptatriene.

An "aryl" group refers to an all-carbon monocyclic or fused-ring polycyclic (i.e., rings which share adjacent pairs of carbon atoms) groups having a completely conjugated pi-electron system. Examples, without limitation, of aryl groups are phenyl, naphthalenyl and anthracenyl. The aryl group may be substituted or unsubstituted.

An "aralkyl" group refers to an aryl group that is substituted with an alkyl group. As used herein, when an aralkyl group bonds to some other group, bonding occurs at the aryl group.

An "alkaryl" group refers to an alkyl group that is substituted with an aryl group. As used herein, when an alkaryl group bonds to some other group, bonding occurs at the alkyl group.

As used herein, the terms "selective," "selectively," "substantially," "essentially," "uniformly" and the like, mean that the indicated event occurs to a particular degree. For example, the percent incorporation of a modified nucleotide herein is characterized as "substantially complete." As used herein, this means greater than 90%, preferably greater than 95% and, most preferably, greater than 99%. With regard to cleavage at a modified nucleotide, "selectively" means greater than 10 times, preferably greater than 25 times, most preferably greater than 100 times that of other natural or modified nucleotide(s) in the modified polynucleotide. The percent cleavage at a modified nucleotide is also referred to herein as being "substantially complete." This means greater than 90%, preferably greater than 95%, most preferably greater than 99% complete.

As used herein, an "individual" refers to any higher life form including reptiles, fish, birds and mammals. In particular, the term refers to human beings. However, the methods of this invention are useful for the analysis of the nucleic acids of any living organism.

Discussion

The methods of this invention can be used to examine the genetic DNA of an individual displaying symptoms of a particular disease or disorder known or suspected to be genetically based. Comparison of the DNA of the individual with that of healthy members of the same population will confirm whether the individual is afflicted with a particular genetically-related disease or disorder. The method can also be used to examine an individual displaying symptoms of a disease or disorder of unknown origin to determine if it has a genetic component.

Particularly useful aspects of the methods described herein are ease of assay design, low cost of reagents and suitability of the cleavage products for detection by a variety of methods including, without limitation, electrophoresis, mass spectrometry and fluorescent detection.

a. Base-Modified Nucleotides

A base-modified nucleotide refers to a nucleotide having a chemically modified adenine, cytosine, guanine or thymine (or, in the case of RNA, uracil). A modified polynucleotide is selectively cleavable at the sites of incorporation of the base-modified nucleotide in comparison to sites of incorporation of natural nucleotides. The base-modified nucleotides of this invention are shown in the Summary, above.

Cleavage of polynucleotides into which the base-modified nucleotides of this invention have been incorporated is accomplished using chemical base. Amine chemical bases, such as diethylamine, dipropylamine and pyrrolidine, are presently preferred chemical bases. Amines having boiling points in excess of about 100° C. at atmospheric pressure are particularly preferred. While this includes primary amines with the requisite boiling point, such as, without limitation, 6-hydroxyhexylamine, secondary amines are presently particularly preferred chemical bases. While not being bound to any particular theory, it appears that this might be due to the fact that lower boiling secondary amines volatize at the relatively high temperatures used to obtain greater than 90% cleavage, i.e., 80° C. or higher, thus making it difficult to maintain an optimal concentration of the amine in the cleavage reaction. Examples of higher boiling secondary amines include, without limitation, dibutylamine, piperidine, 3-pyrrolidinol, hexamethyleneimine, morpholine and pyrazine. Secondary amines having a boiling point above 150° C. are even more preferable, with those having a boiling point above 200° C. being the presently most preferred. Such secondary amines include, without limitation, heptamethyleneimine, 3-pyrrolidinol, 2-pyrrolidinemethanol, 3-pyrrolidinemethanol, proline, picolinic acid, piperazine-2-carboxylic acid, 4-piperidineethanol, isonipecotic acid and piperidine-4-carboxlic acid polymine resin (polystyrene). 3-Pyrrolidinol, 2-pyrrolidinemethanol, 3-pyrrolidinemethanol and 4-piperidineethanol are presently preferred high boiling secondary amines for use in the methods of this invention.

When cleavage at a modified base of this invention is carried out in the presence of a phosphine and a chemical base, a unique adduct forms. For example, when the phosphine is, without limitation, tris(2-carboxyethyl) phosphine (TCEP), mass spectrometry of the product is consistent with a structure having a ribose-TCEP adduct at its 3' end and a phosphate moiety at its 5' end:

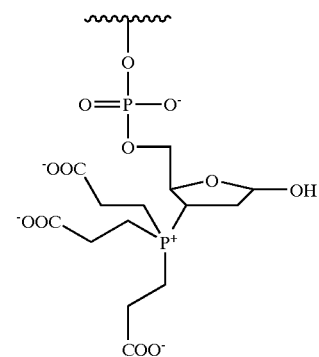

The mechanism of formation of the phosphine adduct is not presently known; however, without being held to any particular theory, a possible mechanism is the following:

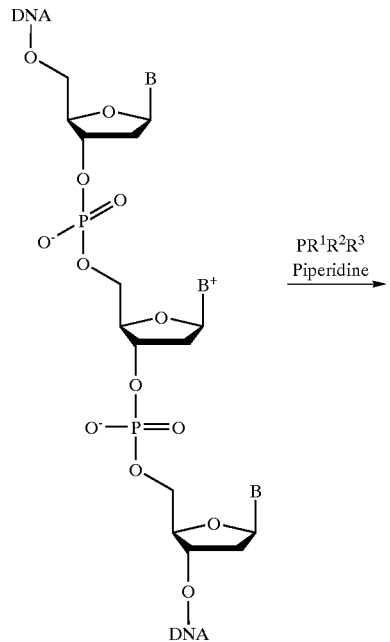

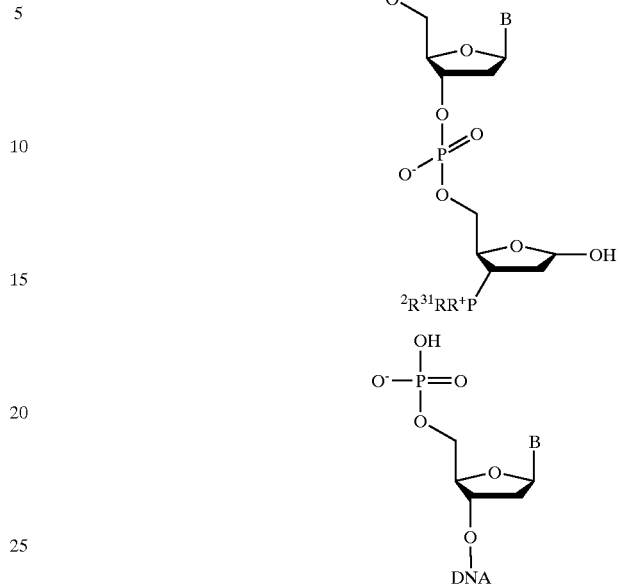

The incorporation of a phosphine into the cleavage product can be used to label polynucleotide fragments at the same time cleavage is being performed. Thus, by using a phosphine that contains a label or tag but is still capable of forming the above-described adduct, such moieties as, without limitation, mass tags, fluorescence tags, radioactive tags and ion-trap tags could be incorporated directly into polynucleotide fragments during cleavage.

While other phosphines useful in the cleavage/tagging procedure described above will become apparent to those skilled in the art based on the disclosures herein, TCEP is presently preferred. The carboxyl (—C(O)OH) groups of TCEP can be readily modified, for example, without limitation, by reaction with an amine, alcohol or mercaptan in the presence of a carbodiimide to form an amide, ester or mercaptoester:

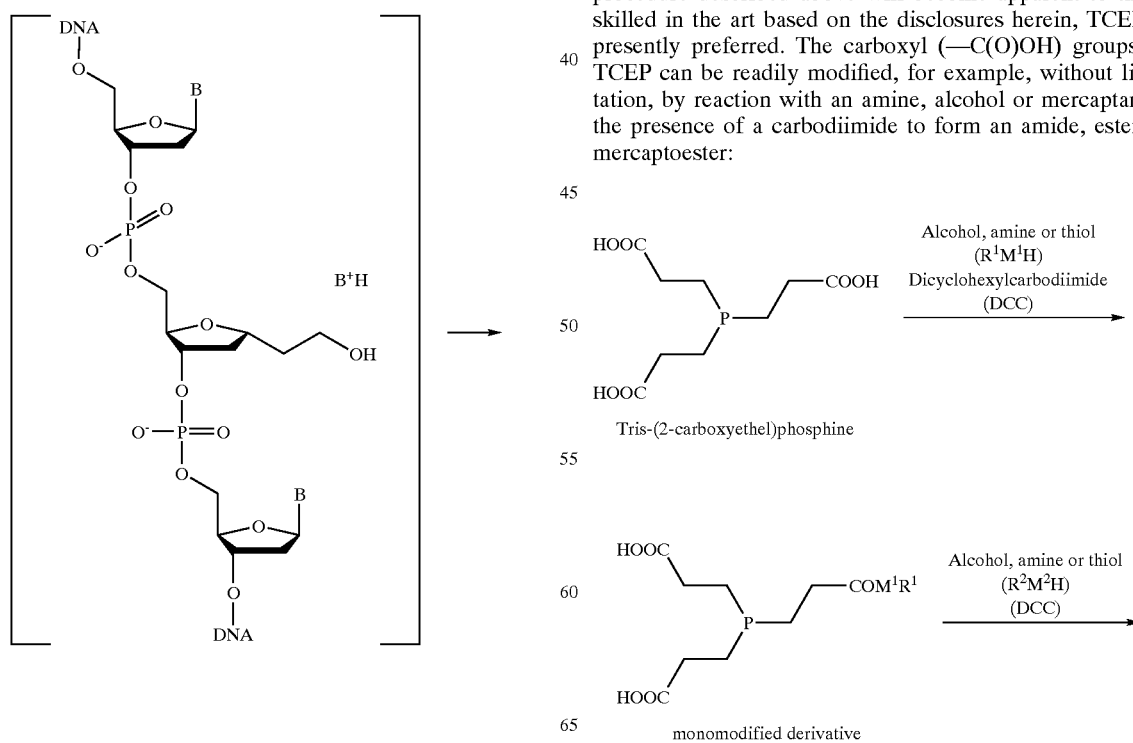

-continued

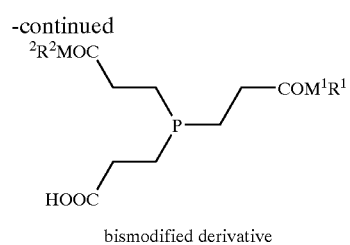

bismodified derivative wherein, $M^1$ and $M^2$ are independently O, NH, NR, S. $R^1$ and $R^2$ are mass tags, fluorescent tags, radioactive tags, ion trap tags or combinations thereof.

When a carboxyl group is reacted with a carbodiimide in the absence of a nucleophile, the product may rearrange to form a stable N-acylurea. If the carbodiimide contains a fluorophore, the resultant phosphine will then carry that fluorophore:

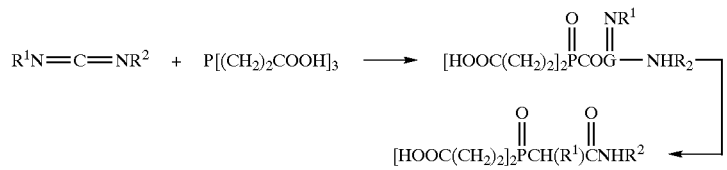

Amino group-containing fluorophores such as fluoresceinyl glycine amide, (5-aminoacetamido)fluorescein, 7-amino-4-methylcoumarin, 2-aminoacridone, 5-aminofluorescein, 1-pyrenemethylamine and 5-aminoeosin may also be used to prepare labeled phosphines. Amino derivatives of lucifer yellow and Cascade Blue can also be employed, as can amino derivatives of biotin. In addition, hydrazine derivatives such as rhodamine and Texas Red hydrazine may be useful in this method. Fluorescent diazoalkanes, such as, without limitation, 1-pyrenyldiazomethane, may be used to form esters with TCEP. Fluorescent alkyl halides may also react with the carboxylate anion (—C(0)O⁻) of the phosphine to form esters. Such halides include, without limitation, panacyl bromide, 3-bromoacetyl-7-diethylaminocoumarin, 6-bromoacetyl-2-diethylaminonaphthalene, 5-bromomethylfluorescein, BODIPY® 493/503 methyl bromide, monobromobimanes and iodoacetamides such as coumarin iodoacetamide. Naphthalimide sulfonate ester reacts rapidly with the anions of carboxylic acids in acetonitrile to give adducts which are detectable by absorption at 259 nm down to 100 femtomoles and by fluorescence at 394 nm down to four femtomoles. There are, furthermore, countless amine-reactive fluorescent probes known in the art. TCEP can be converted into a primary amine by, for example, the following reaction:

The aminophosphine can then reacted with an amine-reactive fluorescent probe for use in the cleavage/labeling method described above.

Many other phosphines and methods for appending tags to them will become apparent to those skilled in the art based on the disclosures herein. Such phosphines, labels and labeling methods are within the scope of this invention.

b. Sugar Modification and Cleavage

Modification of the sugar portion of a nucleotide may also afford a modified polynucleotide that is selectively cleavable at the site(s) of incorporation of such modified nucleotides. In general, the sugar is modified with one or more functional groups that render the 3' and/or the 5' phosphate ester linkage more susceptible to cleavage than the 3' or 5' phosphate ester linkage of the corresponding natural nucleotide. The following are examples, without limitation, of modified sugar nucleotides of this invention. Other sugar modifications will become readily apparent to those skilled in the art in light of the disclosures herein and are therefore deemed to be within the scope of this invention.

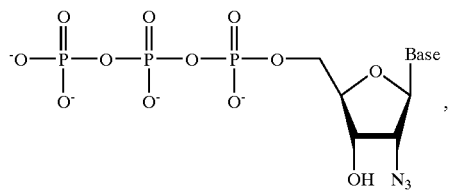

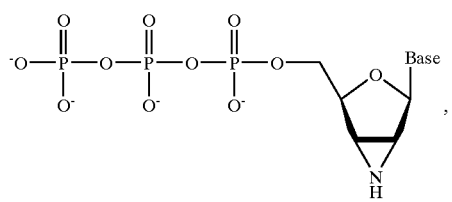

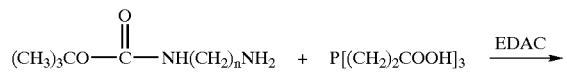

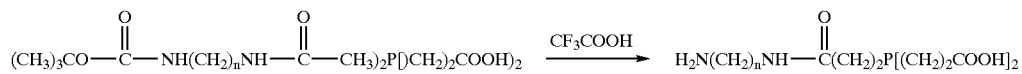

-continued

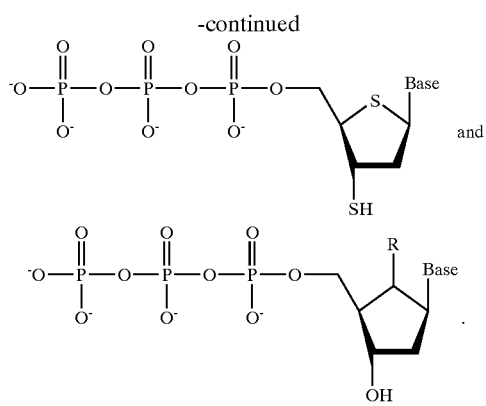

Base is A, C, G, T, U or I. R is —CN, N₃, —SH, —CH₂CN, CH₂OH or —CH₂SH. Cleavage is normally accomplished using acid or chemical base. Treatment with a chemical oxidant or a reducing agent may be required prior to contact with acid or chemical base. Presently preferred acids are dilute inorganic acids, such as, without limitation, dilute hydrochloric acid, dilute sulfuric acid and phosphoric acid. Relatively mild organic acids such as, without limitation, acetic acid may also be used. Presently preferred chemical bases are dilute inorganic bases such as dilute sodium hydroxide, dilute potassium hydroxide and ammonium hydroxide. Non-aqueous bases such as sodium methoxide or ethoxide may also be used. The choice of acid or base to use can be readily determined by those skilled in the art based on the disclosure herein.

c. Fragment Analysis

Analysis of the fragments obtained from the cleavage of a modified polynucleotide can be accomplished in a number of ways including, without limitation, electrophoresis, mass spectrometry, inter- or intra-molecular hybridization and FRET. A presently preferred method is mass spectrometry.

d. Mass Spectrometry

Mass spectrometry is a presently preferred analytical tool for the method of this invention due to its speed, accuracy, reproducibility, low cost and potential for automation (Fu, D. J., et al., *Nature Biotechnology*, 1998, 16:381–384). When detection of a variance in two or more related polynucleotides is the goal, the ability of mass spectrometry to differentiate masses within a few, even one, atomic mass unit (amu) permits such detection without the need for determining the complete nucleotide sequences of the polynucleotides being compared. The required information is obtained from the masses of the fragments.

Mass spectrometric identification of a variance depends on the unique masses of the four deoxynucleotides and their oligomers. Table 1 shows the mass differences among the four deoxynucleotide monophosphates. In Panel A, the masses of the four deoxynucleotide residues are shown across the top, and calculated molecular weight differences between each pair of nucleotide residues are shown in the table. It is understood that the base-modified nucleotides of this invention will have different masses than those shown above for the natural nucleotides. Thus the mass differences will also be different. In general, the mass difference between a base-modified nucleotide and the natural nucleotides in Table 1 will be larger, which should improve mass spec analysis. For example, in Panel B the mass differences between the natural nucleotides and 2-chloroadenine are shown (far right column). The smallest mass difference is 17.3 Da instead of 9 Da as in panel A, providing a greater degree of discrimination between nucleotides using mass spectrometry.

TABLE 1

|  | dAMP | dCMP | dGMP | dTMP | 2-chloro-adenineMP |
|---|---|---|---|---|---|
| Panel A |  |  |  |  |  |
| Mol. Wt. | 313.2 | 289.2 | 329.2 | 304.2 |  |
| vs. dAMP | — | 24 | 16 | 9 |  |
| vs. dCMP |  | — | 40 | 15 |  |
| vs. dGMP |  |  | — | 25 |  |
| Panel B |  |  |  |  |  |
| Mol. wt. | 313.2 | 289.2 | 329.2 | 304.2 | 347.7 |
| vs. dTMP |  |  |  |  | 42.3 |
| vs. dAMP | — | 24 | 16 | 9 | — |
| vs. dCMP |  | — | 40 | 15 | 57.3 |
| vs. dGMP |  |  | — | 25 | 17.3 |

Table 2 shows the calculated masses of all possible 2-mers, 3-mers, 4mers and 5-mers. As can be seen, only two of the 121 oligomers have the same mass. Thus, the nucleotide composition of all 2mers, 3mers, 4mers and all but two 5mers created by cleavage of a polynucleotide can be immediately determined by mass spectrometry, if the instrument has sufficient resolving power. Given the masses in Table 2, an instrument with a resolution (full width at half-maximal height) of 1500 to 2000 would be sufficient. Mass spectrometers with resolution up to 10,000 are commercially available. However, when cleavage is performed at all sites of modified nucleotide incorporation, it is not necessary to consider the masses of all possible 2mers, 3mers, 4mers, etc. because there can be no internal occurrence of the cleavage nucleotide in any fragment. For example, if a modified G (mod G) is the cleavage nucleotide, then all resulting cleavage fragments will have 0 or 1 mod G, depending on retention or loss of mod G in the fragments. If mod G is retained, it must occur at either the 3' or the 5' end of the fragment. Thus, if the cleavage chemistry leaves a mod G on either end of all fragments, then the mass of mod G can be subtracted from the mass of each fragment

TABLE 2

| 2mer | mass | 3mer | Mass | 4mer | mass | 5mer | mass |
|---|---|---|---|---|---|---|---|
| CC | 596 | CCC | 885 | CCCC | 1174 | CCCCC | 1463 |
| CT | 611 | CCT | 900 | CCCT | 1189 | CCCCT | 1478 |
| AC | 620 | CCA | 909 | CCCA | 1198 | CCCCA | 1487 |
| TT | 626 | CTT | 915 | CCTT | 1204 | CCCTT | 1493 |
| AT | 635 | CTA | 924 | CCTA | 1213 | CCCTA | 1502 |
| CG | 636 | CCG | 925 | CCCG | 1214 | CCCCG | 1503 |
| AA | 644 | TTT | 930 | CTTT | 1219 | CCTTT | 1508 |
| GT | 651 | CAA | 933 | CCAA | 1222 | CCCAA | 1511 |
| AG | 660 | TTA | 939 | CTTA | 1228 | CCTTA | 1517 |
| GG | 676 | CTG | 940 | CCTG | 1229 | CCCTG | 1518 |
|  |  | TAA | 948 | TTTT | 1234 | CTTTT | 1523 |
|  |  | CGA | 949 | CAAT | 1237 | CCTAA | 1526 |
|  |  | TTG | 955 | CCAG | 1238 | CCCGA | 1527 |
|  |  | AAA | 957 | TTTA | 1243 | CTTTA | 1532 |
|  |  | TGA | 964 | CTTG | 1244 | CCTTG | 1533 |
|  |  | CGG | 965 | CAAA | 1246 | CCAAA | 1535 |
|  |  | AAG | 973 | TTAA | 1252 | TTTTT | 1538 |
|  |  | TGG | 980 | CTAG | 1253 | CTTAA | 1541 |
|  |  | GGA | 989 | CCGG | 1254 | CCTGA | 1542 |
|  |  | GGG | 1005 | TTTG | 1259 | CCCGG | 1543 |
|  |  |  |  | TAAA | 1261 | TTTTA | 1547 |
|  |  |  |  | CAAG | 1262 | CTTTG | 1548 |
|  |  |  |  | TTAG | 1268 | CAATA | 1550 |

TABLE 2-continued

| 2mer | mass | 3mer | Mass | 4mer | mass | 5mer | mass |
|---|---|---|---|---|---|---|---|
| | | | | CTGG | 1269 | CCAGA | 1551 |
| | | | | AAAA | 1270 | TTTAA | 1556 |
| | | | | TAAG | 1277 | CTTGA | 1557 |
| | | | | CAGG | 1278 | CCTGG | 1558 |
| | | | | TTGG | 1284 | CAAAA | 1559 |
| | | | | AAAG | 1286 | TTTTG | 1563 |
| | | | | TAGG | 1293 | TTAAA | 1565 |
| | | | | CGGG | 1294 | CTAGA | 1566 |
| | | | | AAGG | 1302 | CCGGA | 1567 |
| | | | | TGGG | 1309 | TTTGA | 1572 |
| | | | | AGGG | 1318 | CTTGG | 1573 |
| | | | | GGGG | 1334 | TAAAA | 1574 |
| | | | | | | CAAAG | 1575 |
| | | | | | | TTAAG | 1581 |
| | | | | | | CTGGA | 1582 |
| | | | | | | AAAAA | 1583 |
| | | | | | | CCGGG | 1583 |
| | | | | | | TTTGG | 1588 |
| | | | | | | TAAAG | 1590 |
| | | | | | | CAAGG | 1591 |
| | | | | | | ATTGG | 1597 |
| | | | | | | CTGGG | 1598 |
| | | | | | | AAAAG | 1599 |
| | | | | | | TAAGG | 1606 |
| | | | | | | ACGGG | 1607 |
| | | | | | | TTGGG | 1613 |
| | | | | | | AAAGG | 1615 |
| | | | | | | ATGGG | 1622 |
| | | | | | | CGGGG | 1623 |
| | | | | | | AAGGG | 1631 |
| | | | | | | TGGGG | 1638 |
| | | | | | | AGGGG | 1647 |
| | | | | | | GGGGG | 1663 | and the resulting masses can be compared. The same is, of course, true of A, C and T. Table 3 shows the masses of all 2mers through 7mers lacking one nucleotide. From Table 3, it can be seen that cleavage at A or T consistently produces fragments with larger mass differences between the closest possible cleavage fragments. Cleavage at A produces mass differences of 5, 10, 15, 20 or 25 Da between the closest fragments while cleavage at T affords mass differences of 8, 18 or 24 Da, albeit at the expense of creation of a few more isobaric fragments.

It has been found that, of all oligonucleotides up to the 30mers, only 8 sets of isobaric oligonucleotides (oligonucleotides having masses within 0.01% of each other) exist. These are shown in Table 4. Inspection of Table 4 reveals that every set except

TABLE 3

| Cleavage at G | | | Cleavage at C | | | Cleavage at A | | | Cleavage at T | | |
|---|---|---|---|---|---|---|---|---|---|---|---|
| 2mer | mass | mass Δ | 2mer | Mass | mass Δ | 2mer | mass | mass Δ | 2mer | Mass | mass Δ |
| CC | 517 | | TT | 547 | | CC | 517 | | CC | 517 | |
| CT | 532 | 15 | AT | 556 | 9 | CT | 532 | 15 | AC | 541 | 24 |
| AC | 541 | 9 | AA | 565 | 9 | TT | 547 | 15 | CG | 557 | 16 |
| TT | 547 | 6 | GT | 572 | 7 | CG | 557 | 10 | AA | 565 | 8 |
| AT | 556 | 9 | AG | 581 | 9 | GT | 572 | 15 | AG | 581 | 16 |
| AA | 565 | 9 | CG | 597 | 16 | CG | 597 | 25 | CG | 597 | 16 |
| 3mer | mass | mass Δ | 3mer | Mass | mass Δ | 3mer | mass | mass Δ | 3mer | mass | mass Δ |
| CCC | 806 | | TTT | 851 | | CCC | 806 | | CCC | 806 | |
| CCT | 821 | 15 | TTA | 860 | 9 | CCT | 821 | 15 | CCA | 830 | 24 |
| CCA | 830 | 9 | TAA | 869 | 9 | CTT | 836 | 15 | CCG | 846 | 16 |
| CTT | 836 | 6 | TTG | 876 | 7 | CCG | 846 | 10 | CAA | 854 | 8 |
| CTA | 845 | 9 | AAA | 878 | 2 | TTT | 851 | 5 | CGA | 870 | 16 |
| TTT | 851 | 6 | TGA | 885 | 7 | CTG | 861 | 10 | AAA | 878 | 8 |
| CAA | 854 | 3 | AAG | 894 | 9 | TTG | 876 | 15 | CGG | 886 | 8 |
| TTA | 860 | 6 | TGG | 901 | 7 | CGG | 886 | 10 | AAG | 894 | 8 |
| TAA | 869 | 9 | GGA | 910 | 9 | TGG | 901 | 15 | GGA | 910 | 16 |
| AAA | 878 | 9 | GGG | 926 | 16 | GGG | 926 | 25 | GGG | 926 | 16 |
| 4mer | mass | mass Δ | 4mer | mass | mass Δ | 4mer | mass | mass Δ | 4mer | mass | mass Δ |
| CCCC | 1095 | | TTTT | 1155 | | CCCC | 1095 | | CCCC | 1095 | |
| CCCT | 1110 | 15 | TTTA | 1164 | 9 | CCCT | 1110 | 15 | CCCA | 1119 | 24 |
| CCCA | 1119 | 9 | TTAA | 1173 | 9 | CCTT | 1125 | 15 | CCCG | 1135 | 16 |
| CCTT | 1125 | 6 | TTTG | 1180 | 7 | CCCG | 1135 | 10 | CCAA | 1143 | 8 |
| CCTA | 1134 | 9 | TAAA | 1182 | 2 | CTTT | 1140 | 5 | CCAG | 1159 | 16 |
| CTTT | 1140 | 6 | TTAG | 1189 | 7 | CCTG | 1150 | 10 | CAAA | 1167 | 8 |
| CCAA | 1143 | 3 | AAAA | 1191 | 2 | TTTT | 1155 | 5 | CCGG | 1175 | 8 |
| CTTA | 1149 | 6 | TAAG | 1198 | 7 | CTTG | 1165 | 10 | CAAG | 1183 | 8 |
| TTTT | 1155 | 6 | TTGG | 1205 | 7 | CCGG | 1175 | 10 | AAAA | 1191 | 8 |
| CAAT | 1158 | 3 | AAAG | 1207 | 2 | TTTG | 1180 | 5 | CAGG | 1199 | 8 |
| TTTA | 1164 | 6 | TAGG | 1214 | 7 | CTGG | 1190 | 10 | AAAG | 1207 | 8 |
| CAAA | 1167 | 3 | AAGG | 1223 | 9 | TTGG | 1205 | 15 | CGGG | 1215 | 8 |
| TTAA | 1173 | 6 | TGGG | 1230 | 7 | CGGG | 1215 | 10 | AAGG | 1223 | 8 |
| TAAA | 1182 | 9 | AGGG | 1239 | 9 | TGGG | 1230 | 15 | AGGG | 1239 | 16 |
| AAAA | 1191 | 9 | GGGG | 1255 | 16 | GGGG | 1255 | 25 | GGGG | 1255 | 16 |

TABLE 3-continued

| Cleavage at G | | | Cleavage at C | | | Cleavage at A | | | Cleavage at T | | |
|---|---|---|---|---|---|---|---|---|---|---|---|
| 5mer | mass | mass Δ | 5mer | mass | mass Δ | 5mer | mass | mass Δ | 5mer | mass | mass Δ |
| CCCCC | 1384 | | TTTTT | 1459 | | CCCCC | 1384 | | CCCCC | 1384 | |
| CCCCT | 1399 | 15 | TTTTA | 1468 | 9 | CCCCT | 1399 | 15 | CCCCA | 1408 | 24 |
| CCCCA | 1408 | 9 | TTTAA | 1477 | 9 | CCCTT | 1414 | 15 | CCCCG | 1424 | 16 |
| CCCTT | 1414 | 6 | TTTTG | 1484 | 7 | CCCCG | 1424 | 10 | CCCAA | 1432 | 8 |
| CCCTA | 1423 | 9 | TTAAA | 1486 | 2 | CCTTT | 1429 | 5 | CCCGA | 1448 | 16 |
| CCTTT | 1429 | 6 | TTTGA | 1493 | 7 | CCCTG | 1439 | 10 | CCAAA | 1456 | 8 |
| CCCAA | 1432 | 3 | TAAAA | 1495 | 2 | CTTTT | 1444 | 5 | CCCGG | 1464 | 8 |
| CCTTA | 1438 | 6 | TTAAG | 1502 | 7 | CCTTG | 1454 | 10 | CCAGA | 1472 | 8 |
| CTTTT | 1444 | 6 | AAAAA | 1504 | 2 | TTTTT | 1459 | 5 | CAAAA | 1480 | 8 |
| CCTAA | 1447 | 3 | TTTGG | 1509 | 5 | CCCGG | 1464 | 5 | CCGGA | 1488 | 8 |
| CTTTA | 1453 | 6 | TAAAG | 1511 | 2 | CTTTG | 1469 | 5 | CAAAG | 1496 | 8 |
| CCAAA | 1456 | 3 | ATTGG | 1518 | 7 | CCTGG | 1479 | 10 | AAAAA | 1504 | 8 |
| TTTTT | 1459 | 3 | AAAAG | 1520 | 2 | TTTTG | 1484 | 5 | CCGGG | 1504 | 0 |
| CTTAA | 1462 | 3 | TAAGG | 1527 | 7 | CTTGG | 1494 | 10 | CAAGG | 1512 | 8 |
| TTTTA | 1468 | 6 | TTGGG | 1534 | 7 | CCGGG | 1504 | 10 | AAAAG | 1520 | 8 |
| CAATA | 1471 | 3 | AAAGG | 1536 | 2 | TTTGG | 1509 | 5 | ACGGG | 1528 | 8 |
| TTTAA | 1477 | 6 | ATGGG | 1543 | 7 | CTGGG | 1519 | 10 | AAAGG | 1536 | 8 |
| CAAAA | 1480 | 3 | AAGGG | 1552 | 9 | TTGGG | 1534 | 15 | CGGGG | 1544 | 8 |
| TTAAA | 1486 | 6 | TGGGG | 1559 | 7 | CGGGG | 1544 | 10 | AAGGG | 1552 | 8 |
| TAAAA | 1495 | 9 | AGGGG | 1568 | 9 | TGGGG | 1559 | 15 | AGGGG | 1568 | 16 |
| AAAAA | 1504 | 9 | GGGGG | 1584 | 16 | GGGGG | 1584 | 25 | GGGGG | 1584 | 16 |

| 6mer | mass | mass Δ | 6mer | mass | mass Δ | 6mer | mass | mass Δ | 6mer | mass | mass Δ |
|---|---|---|---|---|---|---|---|---|---|---|---|
| CCCCCC | 1673 | | TTTTTT | 1763 | | CCCCCC | 1673 | | CCCCCC | 1673 | |
| CCCCCT | 1688 | 15 | TTTTTA | 1772 | 9 | CCCCCT | 1688 | 15 | CCCCCA | 1697 | 24 |
| CCCCCA | 1697 | 9 | TTTTAA | 1781 | 9 | CCCCTT | 1703 | 15 | CCCCCG | 1713 | 16 |
| CCCCTT | 1703 | 6 | TTTTTG | 1788 | 7 | CCCCCG | 1713 | 10 | CCCCAA | 1721 | 8 |
| CCCCTA | 1712 | 9 | TTTAAA | 1790 | 2 | CCCTTT | 1718 | 5 | CCCCAG | 1737 | 16 |
| CCCTTT | 1718 | 6 | TTTTAG | 1797 | 7 | CCCCTG | 1728 | 10 | CCCAAA | 1745 | 8 |
| CCCCAA | 1721 | 3 | TTAAAA | 1799 | 2 | CCTTTT | 1733 | 5 | CCCCGG | 1753 | 8 |
| CCCTTA | 1727 | 6 | TTTAAG | 1806 | 7 | CCCTTG | 1743 | 10 | CCCAAG | 1761 | 8 |
| CCTTTT | 1733 | 6 | TAAAAA | 1808 | 2 | TTTTTC | 1748 | 5 | CCAAAA | 1769 | 8 |
| CCCTAA | 1736 | 3 | TTTTGG | 1813 | 5 | CCCCGG | 1753 | 5 | CCCGGA | 1777 | 8 |
| CCTTTA | 1742 | 6 | TTAAAG | 1815 | 2 | CCTTTG | 1758 | 5 | CCAAAG | 1785 | 8 |
| CCCAAA | 1745 | 3 | AAAAAA | 1817 | 2 | TTTTTT | 1763 | 5 | CCCGGG | 1793 | 8 |
| TTTTTC | 1748 | 3 | TTTGGA | 1822 | 5 | CCCTGG | 1768 | 5 | CAAAAA | 1793 | 0 |
| CCTTAA | 1751 | 3 | AAAAGT | 1824 | 2 | TTTTCG | 1773 | 5 | CCAAGG | 1801 | 8 |
| CTTTTA | 1757 | 6 | TTAAGG | 1831 | 7 | CCTTGG | 1783 | 10 | CAAAAG | 1809 | 8 |
| CCAAAT | 1760 | 3 | AAAAAG | 1833 | 2 | TTTTTG | 1788 | 5 | CCGGGA | 1817 | 8 |
| TTTTTT | 1763 | 3 | TTTGGG | 1838 | 5 | CCCGGG | 1793 | 5 | AAAAAA | 1817 | 0 |
| CTTTAA | 1766 | 3 | AAAGGT | 1840 | 2 | TTTCGG | 1798 | 5 | AAACGG | 1825 | 8 |
| CCAAAA | 1769 | 3 | ATTGGG | 1847 | 7 | CCTGGG | 1808 | 10 | AAAAAG | 1833 | 8 |
| TTTTTA | 1772 | 3 | AAAAGG | 1849 | 2 | TTTTGG | 1813 | 5 | CCGGGG | 1833 | 0 |
| CTTAAA | 1775 | 3 | TAAGGG | 1856 | 7 | TTCGGG | 1823 | 10 | AACGGG | 1841 | 8 |
| TTTTAA | 1781 | 6 | TTGGGG | 1863 | 7 | CCGGGG | 1833 | 10 | AAAAGG | 1849 | 8 |
| TAAAAC | 1784 | 3 | AAAGGG | 1865 | 2 | TTTGGG | 1838 | 5 | ACGGGG | 1857 | 8 |
| TTTAAA | 1790 | 6 | AGGGGT | 1872 | 7 | TGGGGC | 1848 | 10 | AAAGGG | 1865 | 8 |
| CAAAAA | 1793 | 3 | AAGGGG | 1881 | 9 | TTGGGG | 1863 | 15 | GGGGGC | 1873 | 8 |
| TTAAAA | 1799 | 6 | GGGGGT | 1888 | 7 | GGGGGC | 1873 | 10 | AAGGGG | 1881 | 8 |
| TAAAAA | 1808 | 9 | AGGGGG | 1897 | 9 | GGGGGT | 1888 | 15 | AGGGGG | 1897 | 16 |
| AAAAAA | 1817 | 9 | GGGGGG | 1913 | 16 | GGGGGG | 1913 | 25 | GGGGGG | 1913 | 16 |

| 7mer | mass | mass Δ | 7mer | mass | mass Δ | 7mer | mass | mass Δ | 7mer | mass | mass Δ |
|---|---|---|---|---|---|---|---|---|---|---|---|
| CCCCCCC | 1962 | | TTTTTTT | 2067 | | CCCCCCC | 1962 | | CCCCCCC | 1962 | |
| CCCCCCT | 1977 | 15 | TTTTTTA | 2076 | 9 | CCCCCCT | 1977 | 15 | CCCCCCA | 1986 | 24 |
| CCCCCCA | 1986 | 9 | TTTTTAA | 2085 | 9 | CCCCCTT | 1992 | 15 | CCCCCCG | 2002 | 16 |
| CCCCCTT | 1992 | 6 | TTTTTTG | 2092 | 7 | CCCCCCG | 2002 | 10 | CCCCCAA | 2010 | 8 |
| CCCCCTA | 2001 | 9 | TTTTAAA | 2094 | 2 | CCCCTTT | 2007 | 5 | CCCCCGA | 2026 | 16 |
| CCCCTTT | 2007 | 6 | TTTTTGA | 2101 | 7 | CCCCCTG | 2017 | 10 | CCCCAAA | 2034 | 8 |
| CCCCCAA | 2010 | 3 | TTTAAAA | 2103 | 2 | CCCTTTT | 2022 | 5 | CCCCCGG | 2042 | 8 |
| CCCCTTA | 2016 | 6 | TTTTAAG | 2110 | 7 | CCCCTTG | 2032 | 10 | CCCCAAG | 2050 | 8 |
| CCCTTTT | 2022 | 6 | TTAAAAA | 2112 | 2 | CCTTTTT | 2037 | 5 | CCCAAAA | 2058 | 8 |
| CCCCTAA | 2025 | 3 | GGTTTTT | 2117 | 5 | CCCCCGG | 2042 | 5 | CCCCGGA | 2066 | 8 |
| CCCTTTA | 2031 | 6 | TTTAAAG | 2119 | 2 | CCCTTTG | 2047 | 5 | CCCAAAG | 2074 | 8 |
| CCCCAAA | 2034 | 3 | TAAAAAA | 2121 | 2 | CTTTTTT | 2052 | 5 | CCAAAAA | 2082 | 8 |
| CCTTTTT | 2037 | 3 | TTTTGGA | 2126 | 5 | CCCCTGG | 2057 | 5 | CCCGGGG | 2082 | 0 |
| CCCTTAA | 2040 | 3 | TTAAAGA | 2128 | 2 | CCTTTTG | 2062 | 5 | CCCGGAA | 2090 | 8 |
| CCTTTTA | 2046 | 6 | AAAAAAA | 2130 | 2 | TTTTTTT | 2067 | 5 | CCAAAGG | 2098 | 8 |
| CCCAAAT | 2049 | 3 | TTTGGAA | 2135 | 5 | CCCTTGG | 2072 | 5 | CCCGGGA | 2106 | 8 |
| CTTTTTT | 2052 | 3 | AAAAAGT | 2137 | 2 | CTTTTTG | 2077 | 5 | CAAAAAA | 2106 | 0 |
| CCTTTAA | 2055 | 3 | GGGTTTT | 2142 | 5 | CCCCGGG | 2082 | 5 | CCAAAGG | 2114 | 8 |
| CCCAAAA | 2058 | 3 | TTAAGGA | 2144 | 2 | CTTTCGG | 2087 | 5 | CAAAAAG | 2122 | 8 |
| TTTTTCA | 2061 | 3 | AAAAAAG | 2146 | 2 | GTTTTTT | 2092 | 5 | CCCGGGG | 2122 | 0 |

TABLE 3-continued

| Cleavage at G | | | Cleavage at C | | | Cleavage at A | | | Cleavage at T | | |
|---|---|---|---|---|---|---|---|---|---|---|---|
| CCTTAAA | 2064 | 3 | TTTGGGA | 2151 | 5 | CCCTGGG | 2097 | 5 | CCGGGAA | 2130 | 8 |
| TTTTTTT | 2067 | 3 | AAAAGGT | 2153 | 2 | CTTTTGG | 2102 | 5 | AAAAAAA | 2130 | 0 |
| TTTTAAC | 2070 | 3 | AATTGGG | 2160 | 7 | CCTTGGG | 2112 | 10 | AAAACGG | 2138 | 8 |
| TAAAACC | 2073 | 3 | AAAAAGG | 2162 | 2 | GGTTTTT | 2117 | 5 | AAAAAAG | 2146 | 8 |
| ATTTTTT | 2076 | 3 | GGGGTTT | 2167 | 5 | CCCGGGG | 2122 | 5 | CCGGGGA | 2146 | 0 |
| TTTAAAC | 2079 | 3 | TAAAGGG | 2169 | 2 | CTTTGGG | 2127 | 5 | AAACGGG | 2154 | 8 |
| CCAAAAA | 2082 | 3 | TTGGGGA | 2176 | 7 | TGGGGCC | 2137 | 10 | AAAAAGG | 2162 | 8 |
| AATTTTT | 2085 | 3 | AAAAGGG | 2178 | 2 | GGGTTTT | 2142 | 5 | CCGGGGG | 2162 | 0 |
| CTTAAAA | 2088 | 3 | AAGGGGT | 2185 | 7 | CTTGGGG | 2152 | 10 | AACGGGG | 2170 | 8 |
| AAATTTT | 2094 | 6 | GGGGGTT | 2192 | 7 | GGGGGCC | 2162 | 10 | AAAAGGG | 2178 | 8 |
| CTAAAAA | 2097 | 3 | AAAGGGG | 2194 | 2 | GGGGTTT | 2167 | 5 | AGGGGGC | 2186 | 8 |
| AAAATTT | 2103 | 6 | AGGGGGT | 2201 | 7 | GGGGGTC | 2177 | 10 | AAAGGGG | 2194 | 8 |
| CAAAAAA | 2106 | 3 | AAGGGGG | 2210 | 9 | GGGGGTT | 2192 | 15 | CGGGGGG | 2202 | 8 |
| AAAAATT | 2112 | 6 | GGGGGGT | 2217 | 7 | CGGGGGG | 2202 | 10 | AAGGGGG | 2210 | 8 |
| AAAAAAT | 2121 | 9 | AGGGGGG | 2226 | 9 | GGGGGGT | 2217 | 15 | AGGGGGG | 2226 | 16 |
| AAAAAA | 2130 | 9 | GGGGGG | 2242 | 16 | GGGGGGG | 2242 | 25 | GGGGGGG | 2242 | 16 |

TABLE 4

| | Polynucleotides | Masses |
|---|---|---|
| Set 1 | d (C$_2$G$_3$) | 1566.016 |
| | d (A$_5$) | 1566.068 |
| Set 2 | d (C$_5$G$_3$) | 2433.584 |
| | d (T$_8$) | 2433.603 |
| | d (C$_3$A$_5$) | 2433.636 |
| Set 3 | d (A$_1$G$_7$) | 2617.707 |
| | d (C$_8$T$_1$) | 2617.711 |
| Set 4 | d (C$_{10}$T$_1$) | 3196.090 |
| | d (G$_{10}$) | 3196.137 |
| Set 5 | d (C$_6$T$_1$A$_4$) | 3292.134 |
| | d (C$_{13}$) | 3292.190 |
| Set 6 | d (C$_{13}$) | 3759.457 |
| | d (T$_7$A$_1$G$_4$) | 3759.472 |
| Set 7 | d (C$_5$T$_9$) | 4183.751 |
| | d (A$_6$G$_7$) | 4183.779 |
| Set 8 | d (T$_7$G$_7$) | 4433.899 |
| | d (C$_{11}$A$_4$) | 4433.936 |

Set 2 involves a polynucleotide with multiple G residues. Thus, cleavage at mod G would eliminate all isobaric masses except one, d(T$_8$) vs d(C$_3$A$_5$) which could not be resolved by mass spectrometry with a resolution of 0.01% However, cleavage at either a mod C or a mod A would resolve the matter.

For a polynucleotide of known sequence, one can easily predict whether cleavage at a particular nucleotide would produce any of the above confounding artifacts and then choose experimental conditions that avoid, reduce or resolve them.

Table 5 shows the sets of mass changes expected on complementary strands for all possible point mutations (transitions and transversions). Whether a particular variance is an addition of a nucleotide (approximately 300+a.u. increase in fragment mass), a deletion of a nucleotide (approximately a 300+a.u. decrease in fragment mass) or a substitution of one nucleotide for another can easily be ascertained. Furthermore, if the variance is a substitution, the exact nature of that substitution can also be determined.

TABLE 5

| | | Resolving Power of MS Instrument (FWHM) | | | |
|---|---|---|---|---|---|
| | | 1,000 | 1,500 | 2,000 | 10,000 |
| Nucleotide substitution | Δ (Da) | Maximum fragment in which Δ at left is resolvable | | | |
| C <-> G | 40 | 123 nt | 184 nt | 246 nt | 1,230 |
| G <-> T | 25 | 77 nt | 116 nt | 154 nt | 770 |
| A <-> C | 24 | 74 nt | 111 nt | 148 nt | 740 |
| A <-> G | 16 | 49 nt | 74 nt | 98 nt | 490 |
| C <-> T | 15 | 46 nt | 69 nt | 92 nt | 460 |
| A <-> T | 9 | 27 nt | 41 nt | 55 nt | 270 |

Table 5 also summarizes the relation between mass spectrometer 4 resolution and nucleotide changes in determining the maximum size fragment in which a given base change can be identified. The maximum size DNA fragment in which a base substitution can theoretically be resolved is provided in the four columns on the right for each possible nucleotide substitution. The mass difference created by each substitution (Δ, measured in Daltons, Da) and the resolving power of the mass spectrometer determine the size limit of fragments that can be successfully analyzed. Presently available commercial MALDI instruments can resolve between 1 part in 1,000 to 1 part in 5,000 while available ESI instruments can resolve 1 part in 10,000. Modified ESI instruments are capable of at least 10-fold greater mass resolution.

e. Cleavage Resistant Modified Nucleotides

The preceding embodiments of this invention relate primarily to the substitution into a polynucleotide of one or more modified nucleotides, which enhance the susceptibility of the polynucleotide to cleavage at the site(s) of incorporation. It is also an aspect of this invention to incorporate a combination of cleavage-resistant and cleavage-sensitive modified nucleotides into a polynucleotide to further enhance selectivity. An example of a modified nucleotide which imparts cleavage resistance is the 2'-fluoro derivative, which has been shown to be substantially less susceptible to fragmentation in a mass spectrometer than the corresponding unsubstituted natural nucleotide.

APPLICATIONS

A number of applications of the methods of the present invention are described below. It is understood that the following are exemplary only and are not intended, nor should they be construed, to limit the scope of this invention in any manner whatsoever. Other applications of the methods described herein will become apparent to those skilled in the art based on the disclosures herein. Such applications are within the scope of this invention.

a. Variance Detection

In one aspect of the present invention at least one natural nucleotide is replaced at substantially each point of occurrence in a polynucleotide with a base-modified nucleotide. This is accomplished by either primer extension, if one strand is being used, or amplification if two strands are being used. The resultant modified polynucleotide is treated with a reagent or combination of reagents that cleaves it at substantially each base-modified nucleotide. Under this protocol, if the abundance of A, C, G and T were equal in naturally-occurring polynucleotides and if their distribution were entirely random, then the fragments obtained would average 4 nucleotides. In actuality, there is considerable deviation in the size of fragments due to the non-random distribution of nucleotides in biological polynucleotides and the unequal amounts of A:T vs. G:C base pairs in different genomes. Furthermore, the modified polynucleotide will not be cleaved until the first occurrence of a modified nucleotide after the end of the primer. Thus, one fragment (if single strand primer extension is used, two if amplification is used) will contain all the primer nucleotides plus those of the modified polynucleotide up to the point of incorporation of the first modified nucleotide. Often, these primer-containing fragments will be the largest produced. This can be advantageous in the design of genotyping assays. That is, primers can be designed so that a suspected polymorphic locus is the first occurrence of a modified nucleotide corresponding to one of a pair of SNP nucleotides after the end of the primer. Thus, only the primer-containing fragment must be analyzed to determine the genotype.

Due to the variation in length of fragments that will be created on cleavage, a mass spectrometer must be capable of detecting the masses of oligonucleotides up to 20mers or even 30mers. To match the expected fragment sizes to the capabilities of the mass spectrometer being used, it is desirable to select an optimal modified nucleotide substitution/cleavage scheme for each polynucleotide sequence that is to be analyzed. One method for accomplishing this is the following:

(a) For each nucleotide at each position in a test polynucleotide, substitute each of the other three nucleotides. For example, if position 1 of the test polynucleotide is an A, hypothetical polynucleotides having T, G and C at position 1 are generated. The same is done for each nucleotide in the polynucleotide. Thus, if the test polynucleotide is 100 nucleotides in length, 300 new hypothetical polynucleotides will be generated if only one strand is being used. If two strands are involved, then another 300 polynucleotides will be generated from the complementary strand.

(b) Generate the masses that would be produced by cleaving at A in the original (reference) polynucleotide and at T, C, G in each of the three new hypothetical polynucleotides obtained by the substitutions of T, C or G for A at position 1. For each of the four cleavages (T, C, G, A), determine whether the disappearance of an existing mass or the generation of a new mass would create a difference in the total set of masses. If a difference is created, determine whether it is a single difference or two differences (i.e. a disappearance of one mass and an appearance of another). Also, determine the magnitude of the mass difference compared to that of the set of masses generated by cleavage of the reference sequence. Perform this same analysis for each of the 100 nucleotides of the original polynucleotide.

(c) Generate a correlation score for each of the four base-specific cleavages. The correlation score increases in proportion to the fraction of the 300 deviations from the reference sequence that produces one or more mass changes (with a higher correlation score being given for two mass differences). The correlation score will also be proportional to the size of the mass differences (larger mass differences score higher).

In the case of primer extension, the analysis is performed for one strand; in the case of amplification, it is carried out for both strands. The method can be extended to combinations of substitution and cleavage. For example, T cleavage on each of the strands of a polynucleotide or cleavage at T and A on one strand (in either case the cleavage may be carried out independently or simultaneously on the two strands) or cleavage of one strand at T and the other at A. Based on the correlation scores for each of the different approaches, an optimal substitution/cleavage scheme for the available instrument can be determined in advance of experimental work.

The above procedure is readily computerized. Furthermore, the program set up to determine the best experimental protocol can also be programmed to perform the comparison of experimental cleavage masses obtained with the hypothetical results, which constitute all possible cleavage masses. That is, the program can be constructed to compare all the masses in the experimentally determined mass spectrum with the cleavage masses expected from cleavage of the reference sequence and to flag any new or missing masses. If there are new or missing masses, the experimental set of masses can be compared with the masses generated in the computational analysis of all the possible nucleotide substitutions, insertions or deletions associated with the experimental cleavage conditions. However, nucleotide substitutions are about ten times more common than insertions or deletions, so an analysis of substitutions alone might suffice. The computational analysis data for all possible nucleotide insertions, deletions and substitutions can be stored in a look-up table. The set of computational masses that matches the experimental data then provides the sequence of the new variant sequence or, at a minimum, the restricted set of possible sequences of the new variant sequence. (The location and chemical nature of a substitution may not be uniquely specified by one cleavage experiment.) To resolve all ambiguity concerning the nucleotide sequence of a variant sample may require, in some cases, another substitution and cleavage experiment or may be resolved by some other sequencing method (e.g. conventional sequencing methods or sequencing by hybridization). It may be advantageous to routinely perform multiple different substitution and cleavage experiments on all samples to maximize the fraction of variances, which then can be precisely assigned.

A computational analysis of natural polynucleotides of 50, 100, 150, 200 and 250 nucleotides has revealed that combinations of two nucleotide cleavages (for example cleave at A on one strand and G on the complementary strand) result in 99–100% detection efficiency, considering all possible substitutions up to 250 nt. Useful data might even be obtainable from fragments up to 1000 nt, although the detection efficiency would in most cases be less than 100%.

b. Genotyping

As DNA sequence data accumulates more and more variances in the genetic code for individuals compared to the general population within a species are being recognized. Some of these variances are being related to phenotypic differences, such as an increased susceptibility to a particular disease of a different reaction to a given therapeutic regime. Thus, there is increasing demand for accurate, high throughput, automatable and inexpensive methods for determining the status of a specific nucleotide or nucleotides in a gene in which a variance between individuals has been discovered. This procedure—the determination of the nucleotide at a particular location in a DNA sequence—is referred to as genotyping. The methods of this invention are well suited to genotyping. First, a segment of DNA in which a variance is known to occur in some individuals is replicated to produce enough of the segment to work with. This can be accomplished by primer extension or by amplification. Amplification by PCR is presently preferred. The amplification is performed in the presence of three natural nucleotides and one base-modified nucleotide. The base-modified nucleotide can correspond to one of the nucleotides giving rise to the variance or it can correspond to a nucleotide that flanks the variable position. The latter approach can in some cases be advantageous because the primer sequence is then never a part of the fragment that contains the polymorphism. This has the advantage of producing low molecular weight fragments, which, in turn, results in more efficient desorption in MALDI mass spec and a larger signal than those obtained from larger fragments. In addition, the higher peaks might allow for enhanced automated calling of variances. However, depending on the length of the fragments predicted by using a flanking nucleotide, it might be more advantageous to use a modified nucleotide that corresponds to one of the nucleotides at the polymorphic site. For example, if an A/T polymorphism is to be genotyped, the cleavable nucleotide could be either A or T. If a G/A polymorphism is to be genotyped the cleavable nucleotide could be either A or G. Conversely the assay could be set up for the complementary strand, where T and C occur opposite A and G. The polymerization product is chemically cleaved by treatment with acid, base or other reagent. If the alleles being studied are heterozygous, two products will be obtained with one being longer than the other as a result of the presence of the cleavable nucleotide at the polymorphic site in one allele but not the other. A mass change, but not a length change, also occurs on the opposite strand. One constraint is that one of the primers used for producing the polynucleotide must be located such that the first occurrence of the cleavable nucleotide after the end of the primer is at the polymorphic site. This usually requires one of the primers to be close to the polymorphic site. An alternative method is to simultaneously incorporate two cleavable nucleotides, one for a polymorphic nucleotide on the (+) strand, one for a polymorphic nucleotide on the (−) strand. For example, one might incorporate cleavable dA on the (+) strand (to detect an A-G polymorphism) and cleavable dC on the (−) strand (to positively detect the presence of the G allele on the (+) strand). In this case, it may be advantageous to have both primers close to the variant site. The two allelic products of different size can be analyzed by, without limitation, electrophoresis, mass spectrometry or FRET analysis. Any of these three assays is compatible with multiplexing by means known in the art.

FRET analysis is particularly useful, especially in light of the previously described phosphine/secondary amine cleavage that can result in the appendage of a —FRET dye to a fragment during the cleavage reaction. One way to perform FRET detection is to introduce a probe with a fluorophore or a quencher that hybridizes differentially to the cleaved strand (representing one allele) compared to the non-cleaved strand (representing the other allele). Such differential hybridization is readily achievable because one strand is longer than the other by at least one, and often several nucleotides. A fluorophore or quenching group is placed on the primer used to produce the cleavable polynucleotide such that a FRET relationship is established between the moiety on the probe and the moiety on the primer. That is, the absorbing and emitting wavelengths of the two moieties are matched and the distance and orientation of the two moieties is correct. A signal will be detected for one allele but not the other when the probe and primer are heated to a temperature that causes denaturation of the shorter alleleprobe hybridization product. For example the primer could be hybridized to the region that is removed by cleavage in one allele but is present in the other allele. When selecting primers for PCR or primer extension one consideration might be to locate the primer so as to maximize the length difference between the two alleles. Other means of maximizing the discrimination would include the use of a "molecular beacon" strategy where the ends of the probe are complementary, and form a stem, except in the presence of the non-cleaved allele where the non-cleaved segment is complementary to the stem of the probe and therefore effectively competes with the formation of intramolecular stems in the probe molecule.

Another way to produce a FRET signal that discriminates between two variant alleles is to incorporate a nucleotide containing a dye that interacts with a dye on the 0 primer. The dye-modified nucleotide is selected such that it is incorporated beyond the primer and the polymorphic site. After cleavage, the nucleotide dye of one allele (cleaved) will no longer be within resonance producing distance of the primer dye while, in the other (uncleaved) allele, the proper distance will be maintained and a FRET will occur. A disadvantage of this method is that it requires a purification step to remove unincorporated dye molecules that can produce a background signal which might interfere with FRET detection. A non-limiting example of the experimental steps involved in carrying out this method are: (1) PCR with dye-labeled primer and either a cleavable modified nucleotide also carrying a dye or one cleavable modified nucleotide and one dye-labeled nucleotide. The dye can be on the cleavable nucleotide if the cleavage mechanism results in separation of the dye from the primer. For instance, in the case of 5'-amino substitution, which results in cleavage proximal to the sugar and base of the nucleotide; (2) cleavage at the cleavable modified nucleotide; (3) purification to remove free nucleotides; and (4) FRET detection.

Another example, a genotyping assay, would begin with PCR using one modified nucleotide along with three natural nucleotides. The PCR primers would be designed such that the polymorphic base is near one of the primers and there is no cleavable base between the primer and the polymorphic base. If the cleavable base is one of the polymorphic bases, the primer-containing cleavage product from that allele will be shorter than the product from the other allele.

Any technique that permits determination of the mass of relatively large molecules without causing non-specific disintegration of the molecules in the process may be used with the methods of this invention. A presently preferred technique is MALDI mass spectroscopy, which is well suited to the analysis of complex mixtures. Commercial MALDI instruments are available which are capable of measuring mass with an accuracy on the order of 0.05 to 0.1%. That is, these instruments are capable of resolving molecules differing in molecular weight by as little as one part in two thousand under optimal conditions. Advances in MALDI MS technology will likely increase the obtainable resolution in the future, thus increasing the utility of this invention. The smallest difference that can occur between two variant strands is an A-T transversion, a molecular weight difference of 9 (Table 5). A MALDI mass spec having a resolution of 2,000 (that is, a machine capable of distinguishing an ion with an m/z (mass/charge) of 2,000 from an ion with an m/z of 2,001) would be able to detect an AT transversion in an approximately 18,000 Dalton sequence. A 'Dalton' is a unit of molecular weight used when describing the size of large molecules; for all intents and purposes it is equivalent to molecular weight. In actual use, the practical resolving power of an instrument may be limited by the isotopic heterogeneity of carbon; i.e., carbon exists in nature as Carbon-12 and Carbon-13, and other factors. Assuming an approximately even distribution of the four nucleotides in a DNA fragment, this translates to detection of an A-T transversion in an oligonucleotide containing about 55 nucleotides. At the other end of the spectrum, a single C-G transversion, which results in a molecular weight difference of 40, could be detected in a 246 nt oligonucleotide by MALDI mass spec.

The size of an oligonucleotide in which an A-T transversion is detectable could be increased by substituting a heavier non-natural nucleotide for either the A or the T, for example by replacing A with 7-methyl-A, thus increasing the molecular weight change to 23. Another possibility would be to substitute 2-chloroadenine, which has a mass of 364.5, for A. It has been shown that 2-chloradenine is readily incorporated into polynucleotides by DNA polymerase from *Thermus aquaticus*. (Hentosh, P. *Anal. Biochem.*, 1992, 201: 277–281). As shown in Table 1, this has a favorable effect on mass differences between all the nucleotides and A. Most importantly, it changes the T-A difference from 9 Da to 42.3 Da.

Table 5 shows the approximate size of an oligonucleotide in which each possible single point mutation could be detected by mass spectrometers of different resolving power without any molecular weight modification.

EXAMPLES

1. Cleavage of Base-Modified Polynucleotide Using Secondary Amines

As noted previously, secondary amines having high boiling points at atmospheric pressure (>100° C., preferably >150° C., most preferably >200° C.) are presently preferred chemical bases for cleaving base-modified polynucleotides. These amines have several advantages. Their high boiling points results in less, if any, of the amine being lost due to volatilization during the cleavage, which provides improved control of stochiometry during cleavage and of purification prior to MALDI-TOF mass spectrometric analysis. In addition, the high boiling amines are substantially less odiferous at the temperatures required for cleavage, i.e., 80° C. or higher, preferably, at present, greater than 90° C. and most preferable at present between 90° and 100° C. Presently preferred high boiling secondary amines include 3-pyrridinol, 2-pyrrolidinemethanol, 3-pyrrolidinemethanol and 4-piperidineethanol.

FIG. 2 shows the results of cleavage of the oligonucleotides shown in FIG. 1 after the four natural nucleotides, A, G, C, and T, have been individually replaced by a corresponding base-modified nucleotide, that is, 7-nitro-7-deaza-dA for A, 7-nitro-7-deaza-dG for G, 5-hydroxy-dC for C and 5-hydroxy-dU for T. In FIG. 2, the underlined nucleotides are the primers used to amplify the polynucleotides. The primers are comprised entirely of natural nucleotides that are not modified and do not participate in any way in the cleavage reaction. Prior to cleavage, the modified polynucleotides were oxidized with potassium permanganate (approximately 2 mM $KMnO_4$ for 5 minutes at room temperature). Cleavage was then accomplished by treating the oxidation products with the indicated secondary amines at 95° C. for one hour. As can be seen in FIG. 2, this resulted in incomplete cleavage. The best result was obtained with 3-pyrridinol. It is thought that this might be due to less steric hindrance than with 2 pyrrolidinemethanol and higher nucleophilicity and basicity than the piperidine compound.

Since the three secondary amines have such high boiling points and, in addition, are relatively water soluble due in part to the hydroxyl groups, use of a higher concentration and higher temperature was considered. Thus, when the same four base-modified polynucleotides were subjected, after oxidation with $KMnO_4$, to 1.46 M 3-pyrridinol for one hour at 98° C., base-modified nucleotide specific, complete cleavage was obtained (FIG. 3). Without being bound to a particular theory, it is suspected that this may be due to less steric hindrance than the 2-pyrrolidinemethanol and better nucleophilicity and basicity than 4-piperidineethanol.

Figure 4:
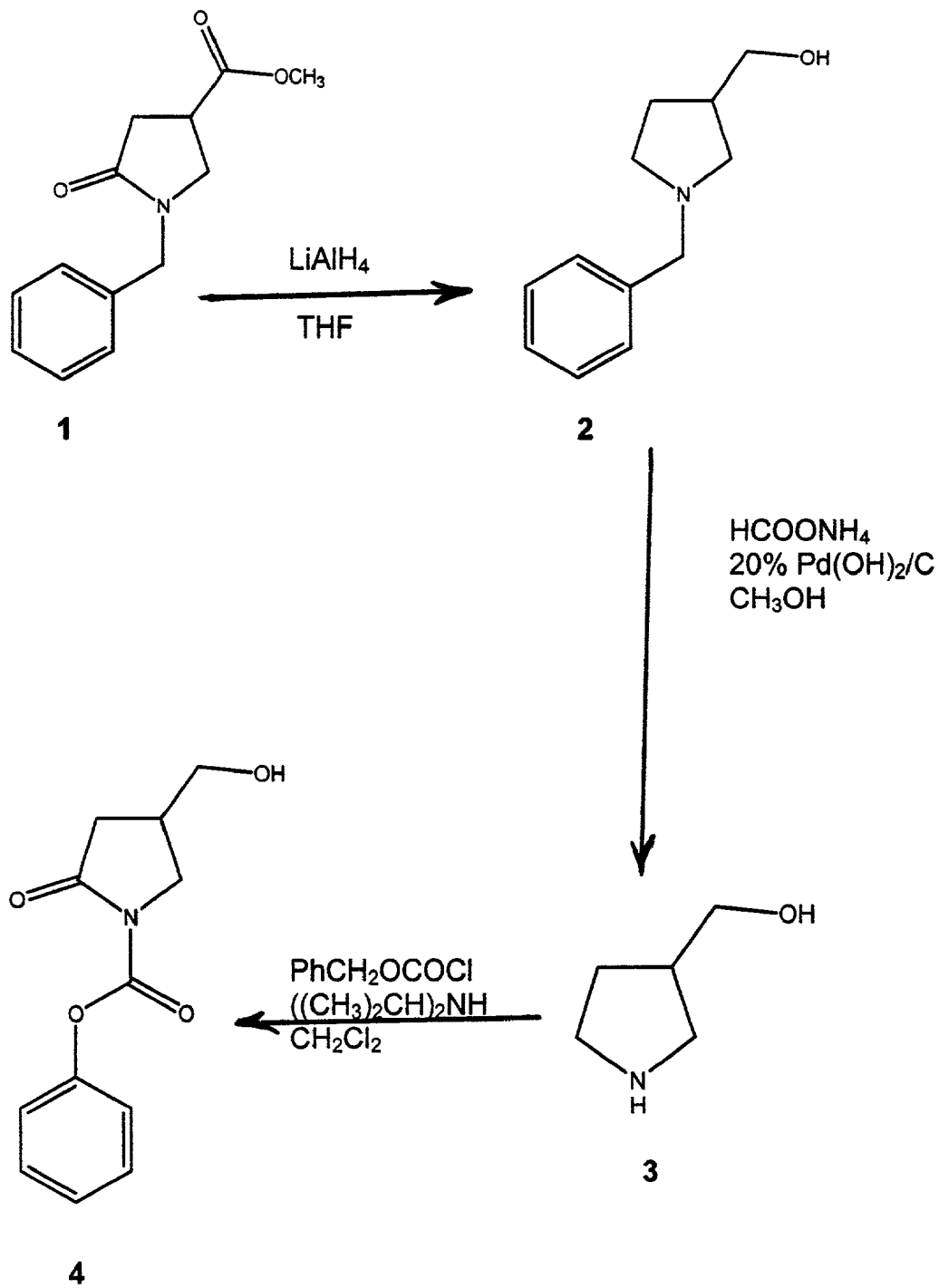
FIG. 4 shows a synthetic route to 3-pyrrolidinemethanol.
Figure 5:
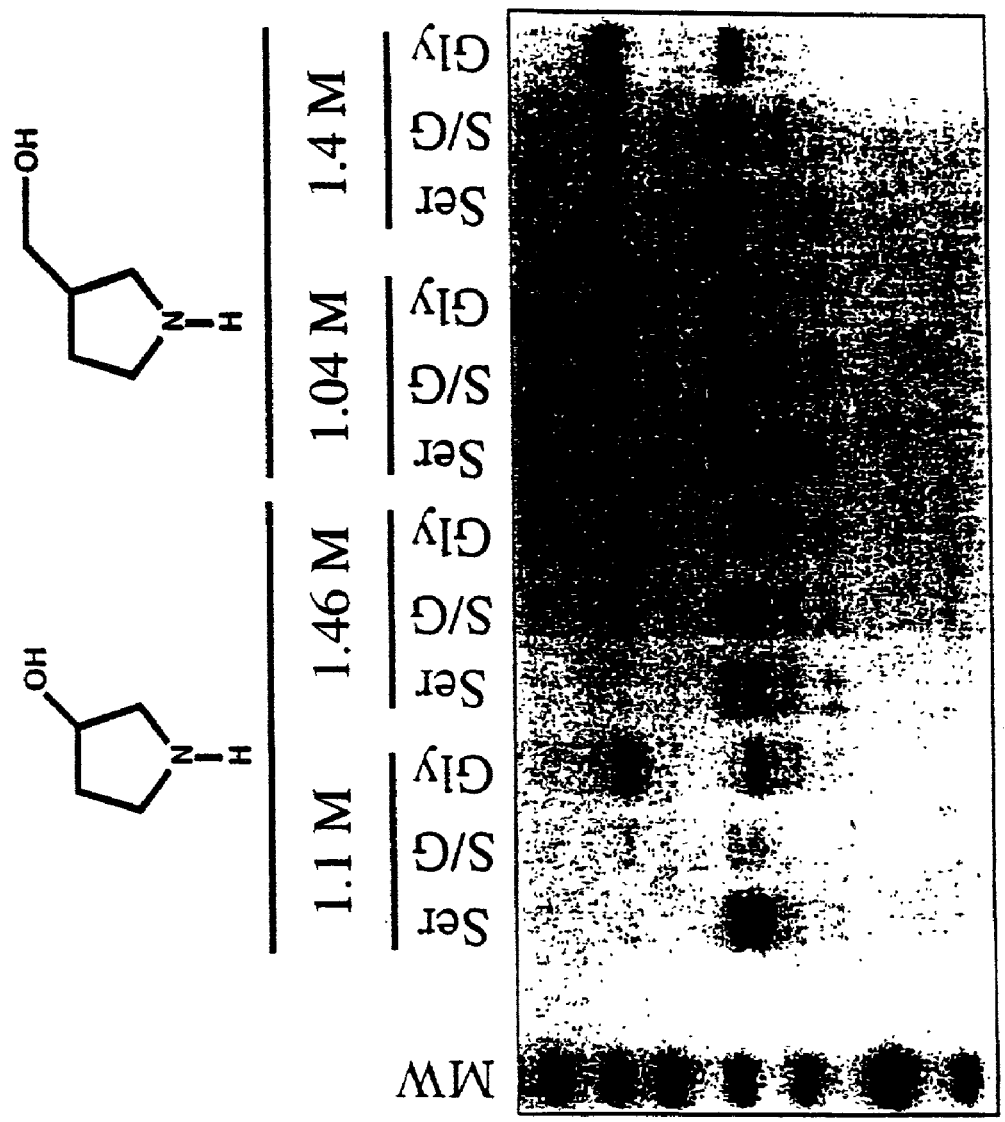
FIG. 5 is a comparison of the results of cleavage of the oligonucleotides depicted in FIG. 1 using 3-pyrrolidinol and 3-pyrrolidinemethanol.

Since the electron-withdrawing effect of hydroxyl groups is generally detrimental to the nucleophilicity and basicity of a secondary amine, it was postulated that positioning this group further from the amino group than in 3-pyrrolidinol might provide an even better cleavage reagent. To avoid potential steric problems, 3-pyrrolidine-methanol was selected as the compound of choice. 3-Pyrrolidinemethanol was synthesized according to the procedure of Goulet et al. ("SRC kinase inhibitor compounds", PCT/US00/17510; WO01/00207 A1), shown in FIG. 4. When the 7-nitro-7-deaza-dA-containing modified polynucleotide was subjected to cleavage using 1.04 M and 1.4 M 3-pyrrolidinemethanol versus 1.1 M and 1.46 M pyrrolidinol at 98° for one hour, the former provided better cleavage results than the latter, even at lower concentrations (FIG. 5). The ability to use a lower concentration of amine may have advantages in subsequent sample preparation prior to mass spectrometry.

2. Genotyping

Figure 6:
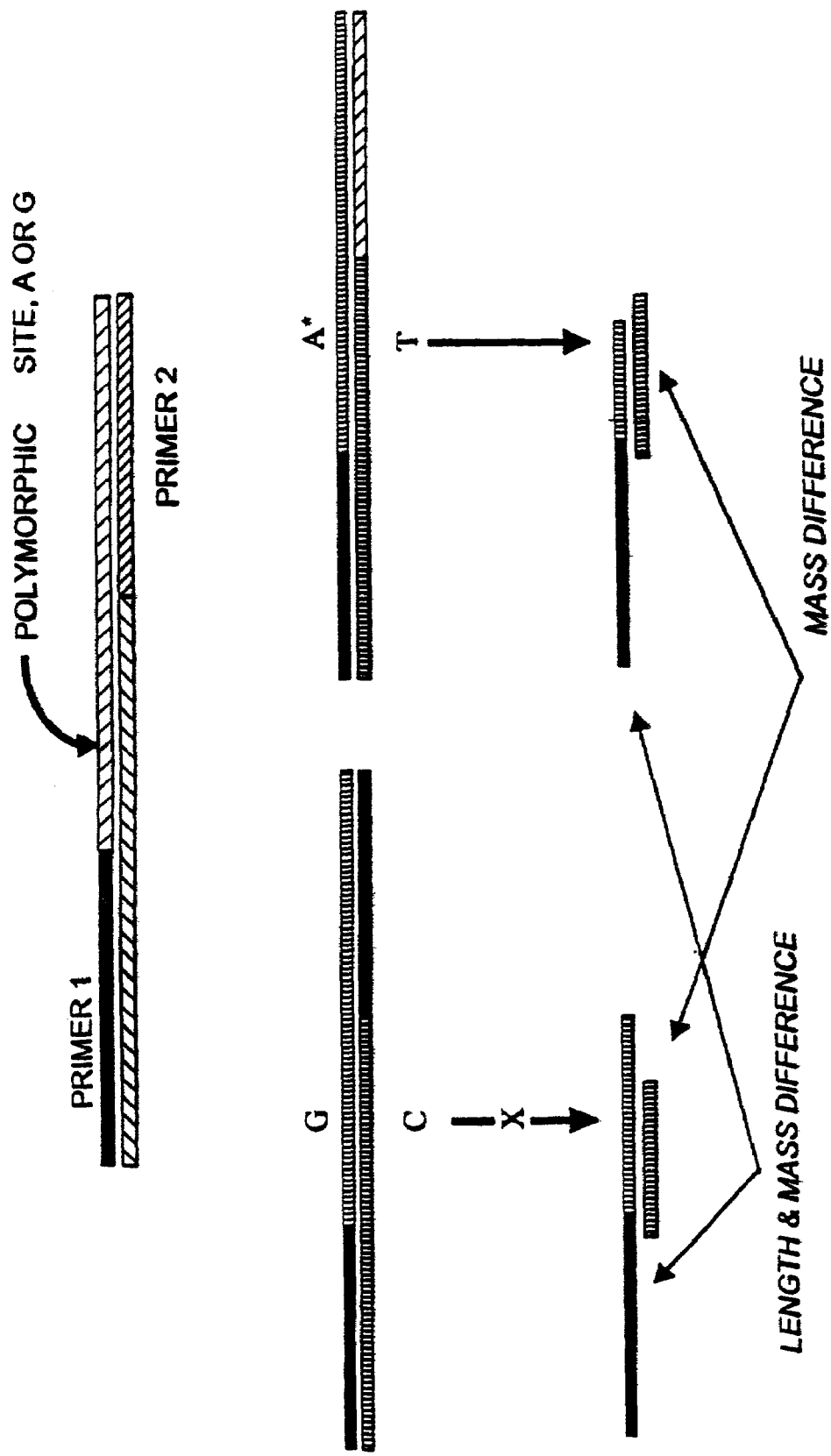
FIG. 6 is a schematic representation of genotyping by chemical cleavage. The template is amplified using one cleavable nucleotide analog, dA*TP. The amplicons are chemically cleaved to give fragments with the indicated length and mass differences. The fragments obtained can be analyzed by mass spec of electrophoresis.

FIG. 6 is a schematic representation of genotyping using the method of this invention. One of the primers (Primer 1) is designed to be close to the polymorphic site so that one of the polymorphic bases (e.g., A), when replaced with a modified nucleotide will be the first cleavage site. PCR amplification with the modified nucleotide and the three natural nucleotides provides the two alleles of which only one would be cleavable at the polymorphic site. Treatment of the cleavable allele with chemical reagents gives a fragment that contains Primer 1. The length of this fragment will reveal the genotype of the sample. Analysis of the fragment can be carried out by, without limitation, mass spectrometry or electrophoresis. Mass spectrometry analysis might also reveal the single base difference on the complementary strand of DNA that contains the polymorphism, providing built-in redundancy and higher accuracy.

Figure 7A:
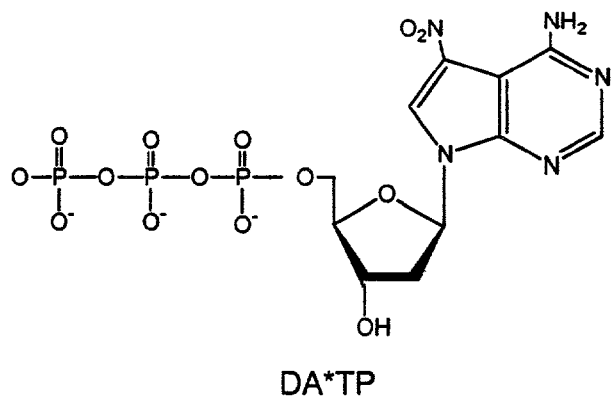
FIG. 7(a) show an 82 bp fragment of transferrin receptor containing the indicated polymorphism [SEQ. IDs 7 and 8], is amplified using a modified nucleotide, dA*TP, the structure of which is shown.
Figure 8:
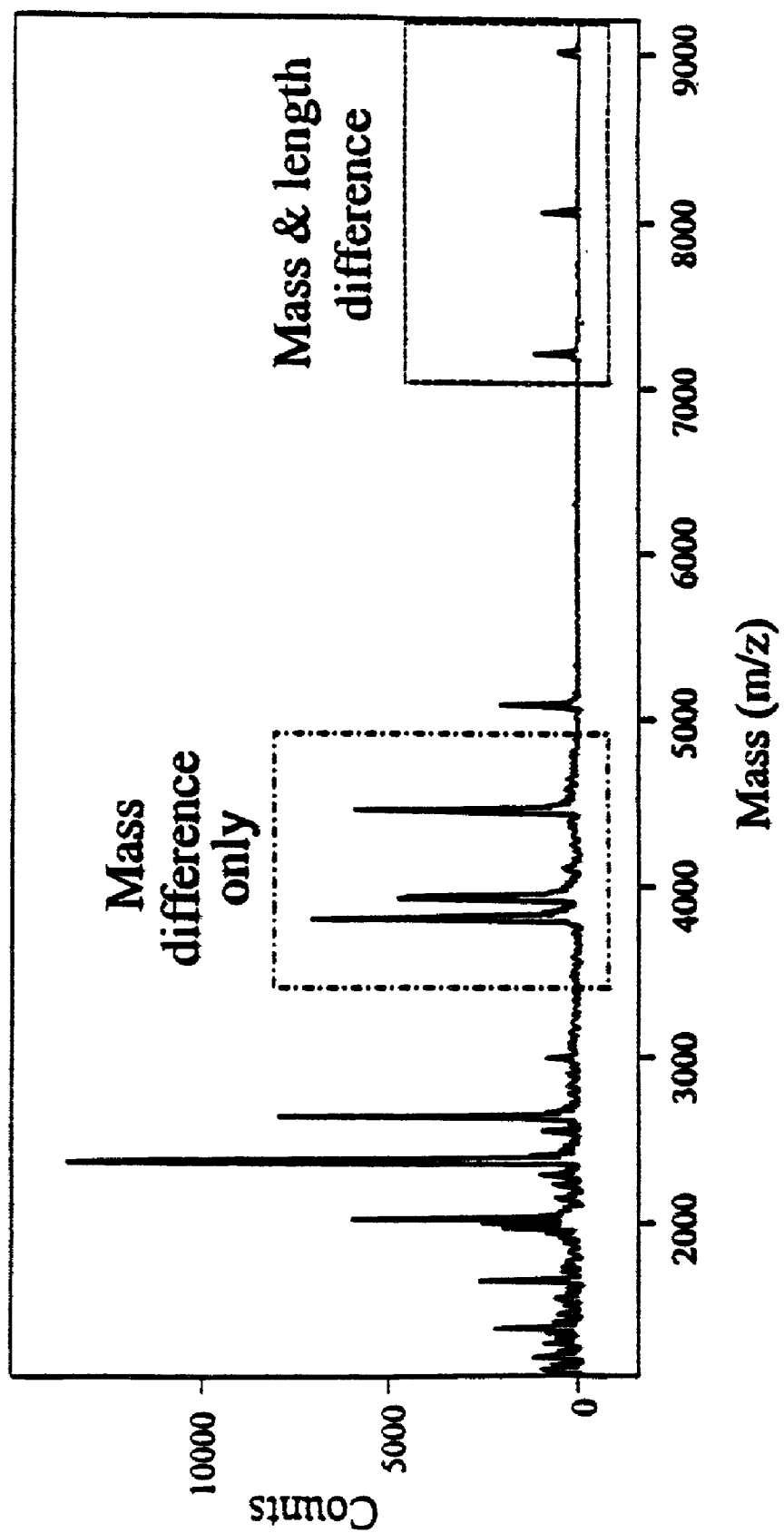
Figure 9:
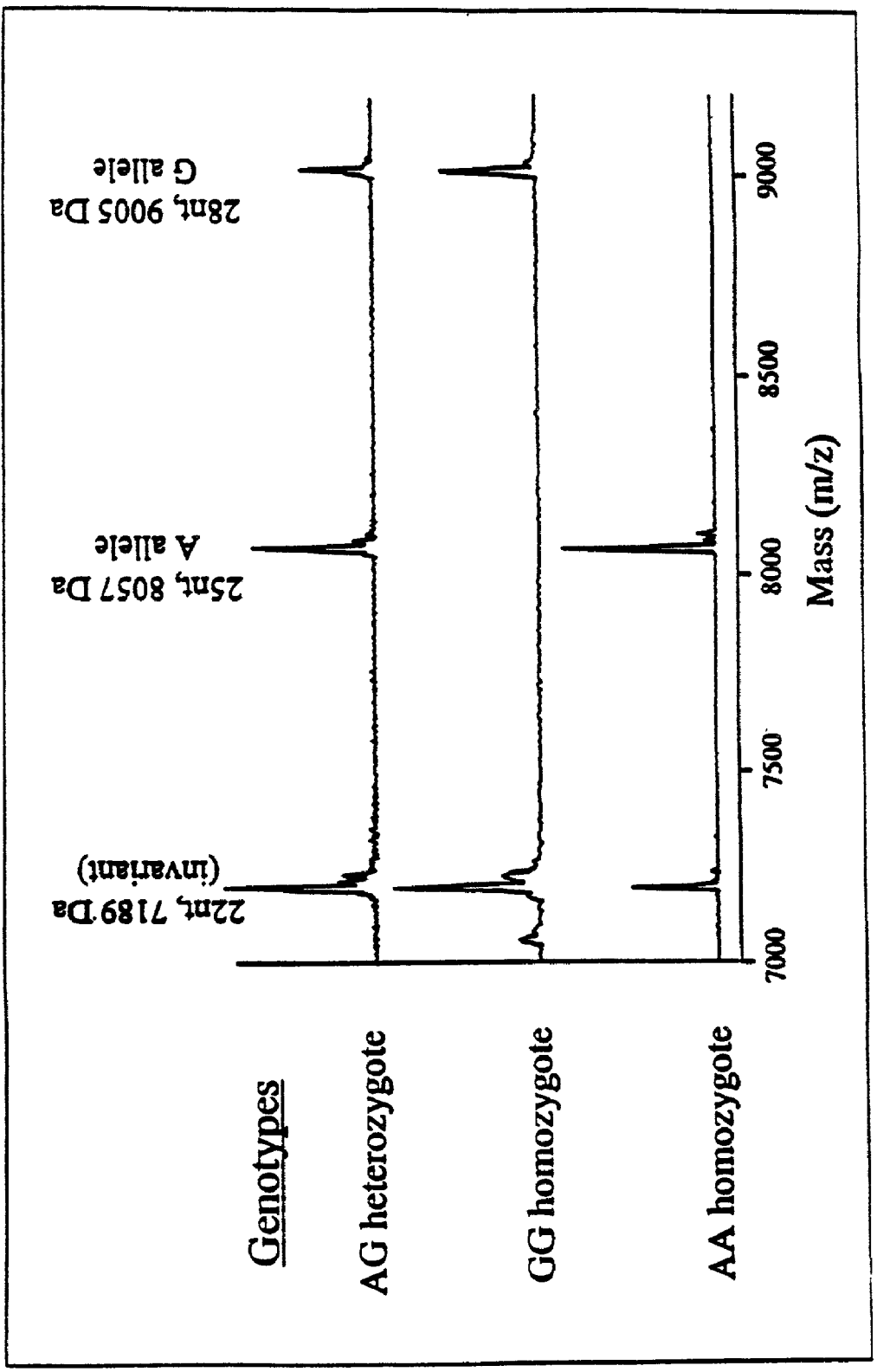

Illustrated in FIGS. 7 to 9 are the chemical cleavage and analysis procedures utilized to genotype transferrin receptor (TR) gene. An 82 bp DNA sequence of TR gene was selected based on the location of the polymorphism and efficiency of amplification (FIG. 7(a)). The polymorphic base (A or G) was positioned 3 bases from the 3' end of Primer 1. For the A allele it is the first modified nucleotide to be incorporated. For the G allele, the first cleavable nucleotide is 6 bases from the primer. As a result, cleavage will produce fragments of different lengths. The PCR amplification reactions (50 µl each) were carried out in standard buffer with polymerase AmpliTaq Gold (0.1 unit/µl) on a Thermocycler (MJ Research PTC-200) using 35 cycles of amplification (1 min denaturation, 1.5 min annealing, and 5 min extension). Analysis of the PCR products on a 5% non-denaturing polyacrylamide gel (stained with Stains-All from Sigma) showed that 7-deaza-7-nitro-dATP can replace dATP and still result in an efficient PCR amplification.

To the PCR products were added piperidine, tris-(2-carboxylethyl)phosphine (TCEP), and Tris base at a final concentration of 1 M, 0.2 M, and 0.5 M, respectively, in a total volume of 100 µl. After incubation at 95° C. for 1 hour, 1 ml of 0.2 M triethylammonium acetate (TEM) was added to each reaction mixture and the resulting solution purified on an OASIS column (Waters). The eluted products were concentrated to dryness on a Speedvac and the residue analyzed by mass spectrometry or electrophoresis. FIG. 7(b) shows the sequences expected from cleavage at 7-deaza-7-nitro-dA. The sequences are grouped according to lengths and molecular weights. The first group contains longer fragments that contain the primer sequence. The 22 nt fragment is invariant and may be used as an internal reference. The 25 nt or 28 nt fragment is expected from the A or G allele, respectively. The shaded group of sequences are from the complementary strand of DNA, including invariant 13 nt and 11 nt fragments that can be used as internal references and a pair of 11 nt fragments expected from two allelic forms of the TR gene with a 15 Da mass difference.

Shown in FIG. 8 is a MALDI-TOF spectrum of chemically cleaved products from an 82 bp heterozygote TR DNA sample. Highlighted in the spectrum are the two regions that contain fragments depicted in FIG. 7(b).

Each purified cleavage sample was mixed with 3-hydroxypicolinic acid and subjected to MALDI-TOF analysis on a Perceptive Biosystems Voyager-DE mass spectrometer. Mass spectra in the region of 7000–9200 Daltons were recorded and the results for the three TR genotypes are shown in FIG. 9. The spectra were aligned using the peak representing the invariant 22 nt fragment (7189 Da). Two additional peaks were observed for the AG heterozygote sample with one corresponding to the A allele (8057 Da) and the other to the G allele (9005 Da). As expected, only one additional peak was observed for the GG or M homozygote samples, each with the molecular weight of cleavage fragments from G or A allele.

Figure 10B:
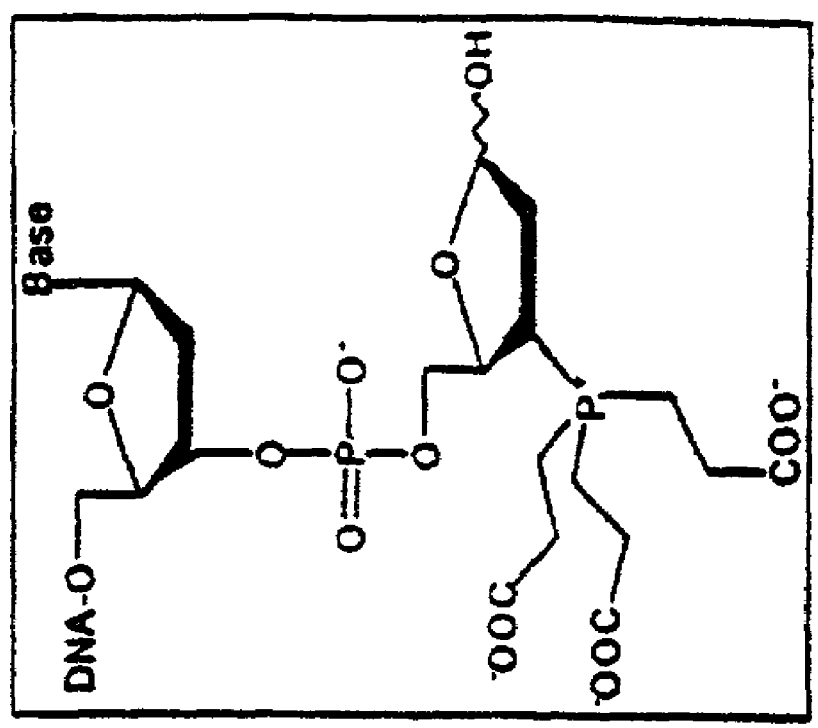

FIG. 10(a) shows a mass spectrum of the AG heterozygote sample in the region of 3700–4600 Da. With 3807 Da and 4441 Da fragments as internal references, the genotype of this sample was confirmed through the observation of two peaks in the middle of the spectrum with 15 Da mass difference. The molecular weights observed by mass spectrometry indicated that phosphate-deoxyribose-TCEP adducts were formed during the cleavage reaction, resulting in fragments that are modified at their 3' ends (FIG. 10(b)).

The data shown in FIGS. 8 and 10 also illustrate that the combination of chemical cleavage and mass spectrometry can provide corroborating genotyping information from both strands of DNA, thereby assuring the accuracy of the analysis.

Figure 11:
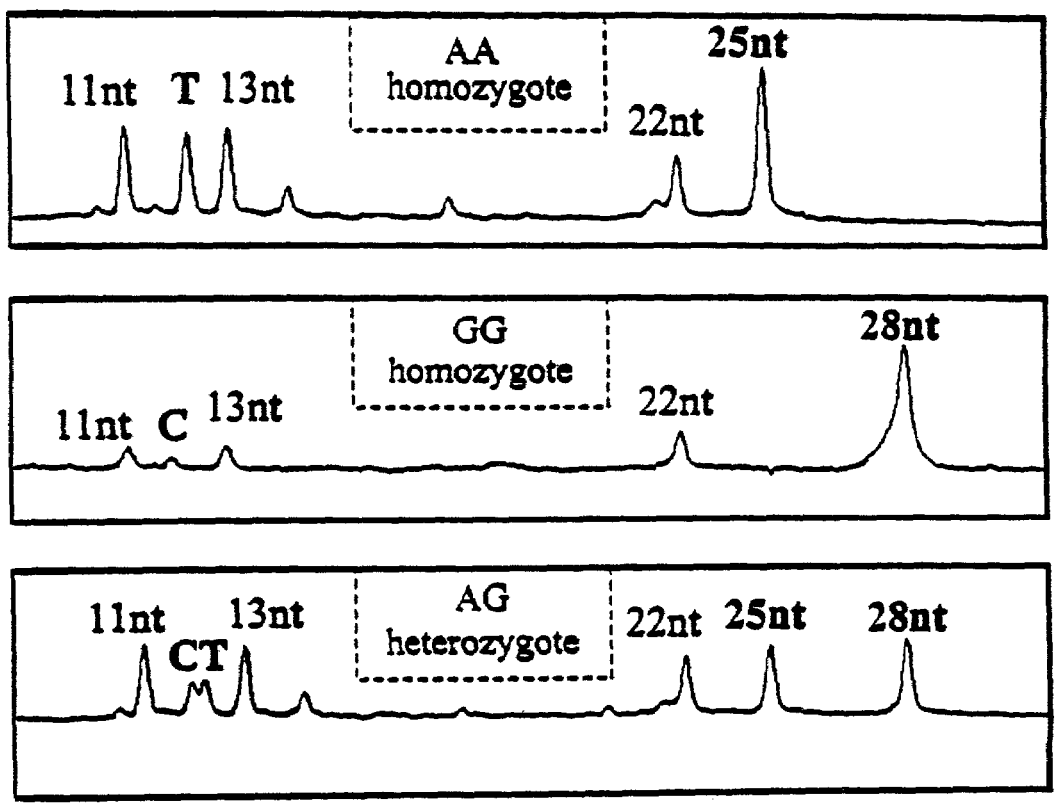
Figure 12:
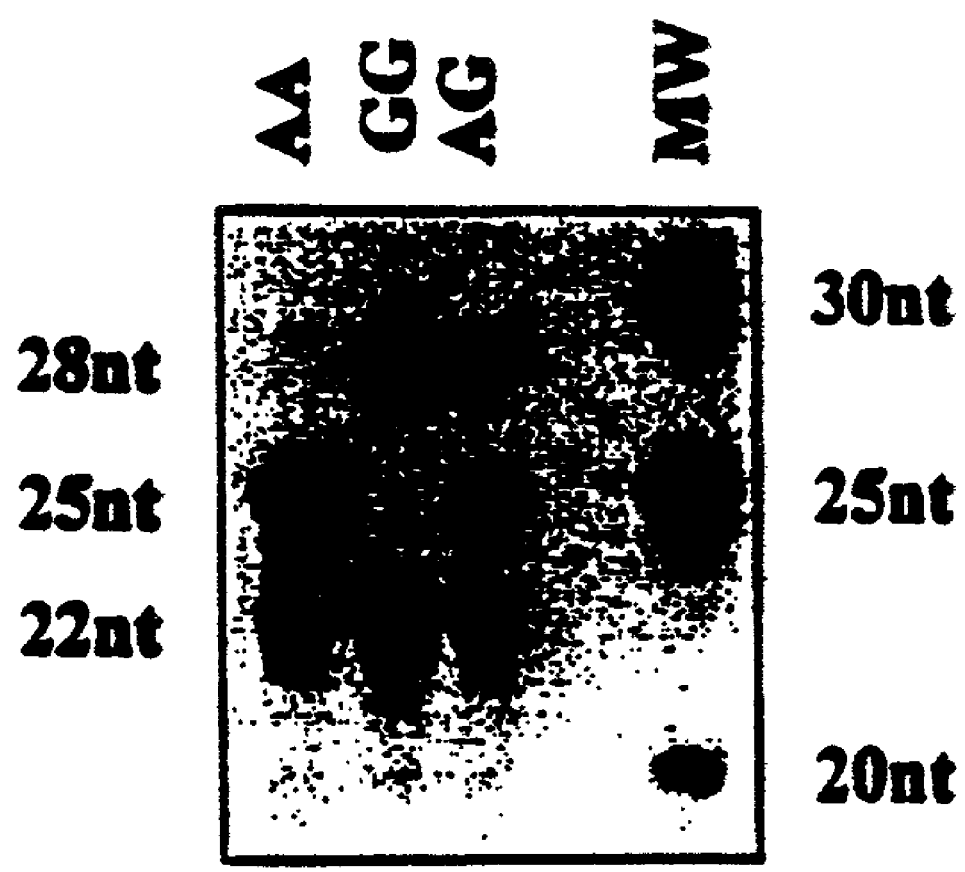

Alternatively, the chemically cleaved samples may be analyzed by electrophoresis. Capillary electrophoresis (CE) analyses were performed using a homemade instrument with a UV detector and a capillary containing denaturing linear polyacrylamide gel. FIG. 11 shows the CE chromatogram obtained from TR samples of various genotypes. As predicted, each genotype gave a different elution pattern corresponding to the lengths of the cleavage products. Whereas the AA homozygote produced a 25 nt fragment and GG homozygote generated a 28 nt fragment, the AG heterozygote sample afforded both 25 nt and 28 nt products. After being labeled at 5' end with $^{32}P$, the cleavage samples were subjected to PAGE analysis. The resulting autoradiogram (FIG. 12) demonstrates that the cleavage is specific with little or no background and the genotyping results are unambiguous.

Another useful detection method for this analysis would be FRET. In fact, FRET has been successfully applied for polymorphism detection using TaqMan® assays (J. A. Todd, et al., 1995, *Nature Genetics*, 3:341–342) and Molecular Beacons (S. Tyagi, et al., 1998, *Nature Biotechnology*, 16:49–53). However, when longer probes are necessary to achieve hybridization to target sequences (e.g., AT rich sequences), it becomes increasingly difficult to distinguish the small difference resulting from a single nucleotide mismatch. The advantage of chemical cleavage in this regard is illustrated in FIG. 13. Similar to the aforementioned example, a modified nucleotide analog of one of the polymorphic bases (e.g., A) is substituted for its natural counterpart in a PCR amplification. Primer 1 is designed to be close to the polymorphic site so that the modified A would be the first cleavable nucleotide in the A allele. Primer 1 is also labeled with a fluorescent group (F1) positioned close to its 3' end (FIG. 13(a)). After amplification and chemical cleavage, a probe covalently attached to another fluorophore F2 (FIG. 13(b)) can be added and the FRET between the two fluorophores measured. Because one of alleles was cleaved closer to the 3' end of primer 1 than the other, the difference in their hybridization is expected to be greater than a single nucleotide mismatch, which may be exploited to distinguish the two alleles. As shown in FIG. 13(c), the temperature can be adjusted so that only the longer fragment obtained from the G allele will hybridize with the probe, resulting in FRET. Since in this system a "NO FRET" result could be interpreted either as allele A or failed PCR amplification, it is necessary to measure the fluorescence of each sample at various temperatures to ensure positive detection of the shorter fragment from allele A at a lower temperature.

CONCLUSION

Thus, it will be appreciated that the method of the present invention provides versatile tools for the detection of polymorphisms among related polynucleotides.

Although certain embodiments and examples have been used to describe the present invention, it will be apparent to those skilled in the art that changes in the embodiments and examples shown may be made without departing from the scope of this invention.

Other embodiments are contained within the following claims.

What is claimed is:

1. A method for detecting a polymorphism in a polynucleotide, comprising:

providing a target polynucleotide;

replacing a natural nucleotide at greater than 90% of its points of occurrence in the target polynucleotide, provided the points of occurrence are not in a primer sequence, by amplification or primer extension using a base-modified nucleotide and three natural nucleotides to give a modified target polynucleotide;

contacting the modified target polynucleotide with a reagent or combination of reagents that cleaves it at greater than 90% of the base-modified nucleotides to give a set of fragments; and, analyzing the fragments to detect a polymorphism, wherein the base-modified nucleotide comprises the following structure:

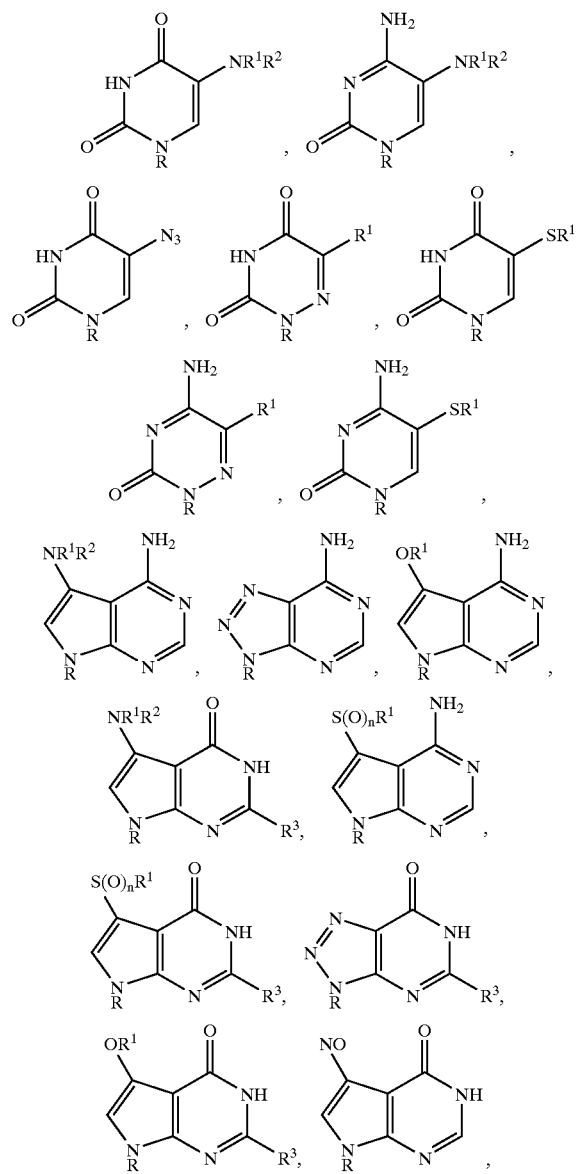

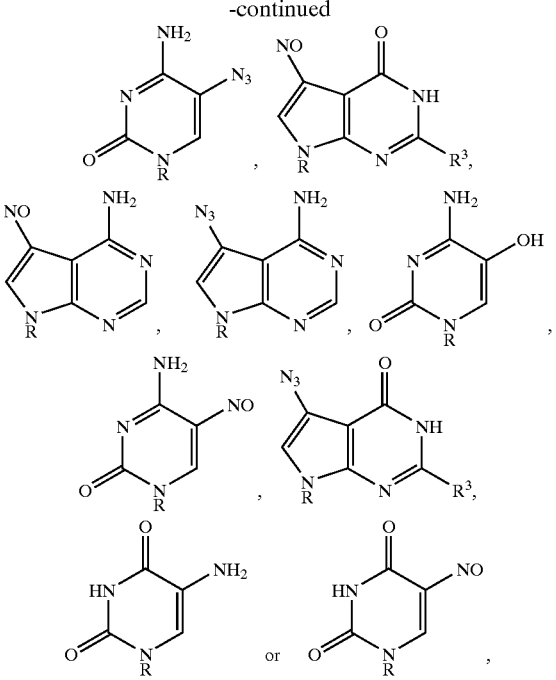

wherein:

R is a ribose or a deoxyribose moiety of a polynucleotide;

$R^1$ and $R^2$ are independently selected from the group consisting of hydrogen, alkyl, cycloalkyl, alkenyl, alkynyl, aryl, aralkyl and alkaryl, wherein, if $R^1$ or $R^2$ contains two or more contiguous methylene (—CH$_2$—) groups, any two such methylene groups may have interjected between them a group selected from the group consisting of —O—, —C(O)NH—, —C(O)NHC(O)—, —NH—, —C(S)NH—, —CO—, —CS—, —S— and (—CF$_2$—)$_m$, wherein m is 1–10;

$R^3$ is hydrogen or —NH$_2$; and, n is 0, 1 or 2.

2. The method of claim 1, wherein the base-modified nucleotide has the chemical structure:

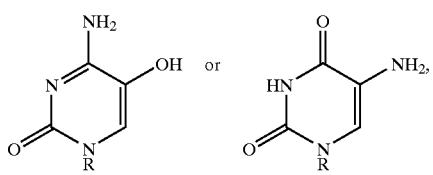

wherein R is a ribose or deoxyribose moiety of an oligonucleotide.

3. The method of claim 2, wherein contacting the modified polynucleotide with a reagent or reagents comprises contacting it with a chemical base.

4. The method of claim 3, wherein the chemical base comprises a secondary amine having a boiling point above 100° C. at atmospheric pressure.

5. The method of claim 4, wherein the secondary amine has a boiling point above 150° C. at atmospheric pressure.

6. The method of claim 4, wherein the secondary amine has a boiling point above 200° C. at atmospheric pressure.

7. The method of claim 6, wherein the secondary amine is selected from the group consisting of 3-pyrrolidinol, 2-pyrrolidinemethanol, 3-pyrrolidinemethanol, 4-hydroxypiperidine and 4-piperidineethanol.

8. The method of claim 1, wherein analysis of the fragments comprises gel electrophoresis.

9. The method of claim 1, wherein analysis of the fragments comprises mass spectrometry.

10. The method of claim 9, wherein mass spectrometry comprise MALDI mass spectrometry.

11. The method of claim 9, wherein in mass spectrometry comprises ESI mass spectrometry.

12. The method of claim 9, wherein analyzing the fragments comprises comparing the masses of the fragments with masses of fragments predicted if the polymorphism is present or with masses of fragments predicted if the polymorphism is not present.

13. A method for detecting a polymorphism in a polynucleotide, comprising:
    replacing a natural nucleotide at greater than 90% of its points of occurrence in the target polynucleotide, provided the points of occurrence are not in a primer sequence, with a modified nucleotide to give a modified target polynucleotide;
    contacting the modified target polynucleotide with a secondary amine having a boiling point greater than 100° C. at atmospheric pressure, at a temperature that results in cleavage of the modified target polynucleotide at greater than 90% of the modified nucleotides to give a set of fragments; and,
    analyzing the fragments to detect a polymorphism.

14. The method of claim 13, wherein the secondary amine has a boiling point greater than 150° C. at atmospheric pressure.

15. The method of claim 13, wherein the secondary amine has a boiling point greater than 200° C. at atmospheric pressure.

16. The method of claim 15, wherein the secondary amine is selected from the group consisting of 3-pyrrolidinol, 2-pyrrolidinemethanol, 3-pyrrolidinemethanol, 4-hydroxypiperidine and 4-piperidineethanol.

17. The method of claim 1 or claim 13, wherein the polynucleotide is contacted with a chemical oxidant prior to contact with the secondary amine.

18. The method of claim 17, wherein the chemical oxidant comprises potassium permanganate.

19. The method of claim 1 or claim 13, wherein the percentage replacement of a natural nucleotide with a modified nucleotide, the percentage cleavage of a modified polynucleotide or both the percentage replacement and the percentage cleavage is greater than 95%.

20. The method of claim 1 or claim 13, wherein the percentage replacement of a natural nucleotide with a modified nucleotide, the percentage cleavage of a modified polynucleotide or both the percentage replacement and the percentage cleavage is greater than 99%.

* * * * *

SEQUENCE LISTING

```
<160> NUMBER OF SEQ ID NOS: 15

<210> SEQ ID NO 1
<211> LENGTH: 69
<212> TYPE: DNA
<213> ORGANISM: Artificial Sequence
<220> FEATURE:
<223> OTHER INFORMATION: Hypothetical sequence prepared to demonstrate
      method of invention.

<400> SEQUENCE: 1
aactggacag cacagacttc accaggcacc atcaagctgc tgaatgaaaa ttcatatgtc    60
cctcgtgag                                                           69

<210> SEQ ID NO 2
<211> LENGTH: 71
<212> TYPE: DNA
<213> ORGANISM: Artificial Sequence
<220> FEATURE:
<223> OTHER INFORMATION: Hypothetical sequence prepared to demonstrate
      method of invention.

<400> SEQUENCE: 2
ctttgacctg tcgtgtctga agtggtccgt ggtagttcga cgacttactt ttaagtatac    60
agggagcact c                                                        71

<210> SEQ ID NO 3
<211> LENGTH: 66
<212> TYPE: DNA
<213> ORGANISM: Artificial Sequence
<220> FEATURE:
<223> OTHER INFORMATION: Hypothetical sequence prepared to demonstrate
      method of invention.

<400> SEQUENCE: 3
ctgaagagaa agttgtcgga gaaactggac agcacagact tcaccaggca ccatcaagct    60
gctgaa                                                              66

<210> SEQ ID NO 4
<211> LENGTH: 65
<212> TYPE: DNA
<213> ORGANISM: Artificial Sequence
<220> FEATURE:
<223> OTHER INFORMATION: Hypothetical sequence prepared to demonstrate
      method of invention.

<400> SEQUENCE: 4
acaactcttt caacagcctc tttgacctgt cgtgtctgaa gtggtccgtg gtagttcgac    60
gactt                                                               65

<210> SEQ ID NO 5
<211> LENGTH: 66
<212> TYPE: DNA
<213> ORGANISM: Artificial Sequence
<220> FEATURE:
<223> OTHER INFORMATION: Hypothetical sequence prepared to demonstrate
      method of invention.
```

-continued

<400> SEQUENCE: 5
tgaagagaaa gttgtcggag aaactggaca gcacagactt cacaggcacc atcaagctgc    60
tgaatg    66

<210> SEQ ID NO 6
<211> LENGTH: 67
<212> TYPE: DNA
<213> ORGANISM: Artificial Sequence
<220> FEATURE:
<223> OTHER INFORMATION: Hypothetical sequence prepared to demonstrate
      method of invention.

<400> SEQUENCE: 6
acaactcttt caacagcctc tttgacctgt cgtgtctgaa gtggtccgtg gtagttcgac    60
gacttac    67

<210> SEQ ID NO 7
<211> LENGTH: 82
<212> TYPE: DNA
<213> ORGANISM: Artificial Sequence
<220> FEATURE:
<223> OTHER INFORMATION: 82 nt sequence from transferrin receptor
      amplified using modified nucleotide.

<400> SEQUENCE: 7
gaaactggac agcacagact tcaccagcac catcaagctg ctgaatgaaa attcatatgt    60
ccctcgtgag gctggatctc aa    82

<210> SEQ ID NO 8
<211> LENGTH: 82
<212> TYPE: DNA
<213> ORGANISM: Artificial Sequence
<220> FEATURE:
<223> OTHER INFORMATION: 82 nt sequence from transferrin receptor with
      polymorphism amplified with modified nucleotide.

<400> SEQUENCE: 8
ctttgacctg tcgtgtctga agtggtcgtg gtagttcgac gacttacttt taagtataca    60
gggagcactc cgacctagag tt    82

<210> SEQ ID NO 9
<211> LENGTH: 25
<212> TYPE: DNA
<213> ORGANISM: Artificial Sequence
<220> FEATURE:
<223> OTHER INFORMATION: Fragment obtained from cleavage of sequence in
      Fig. 7A.

<400> SEQUENCE: 9
gaaactggac agcacagact tcacc    25

<210> SEQ ID NO 10
<211> LENGTH: 28
<212> TYPE: DNA
<213> ORGANISM: Artificial Sequence
<220> FEATURE:
<223> OTHER INFORMATION: Fragment obtained from cleavage of sequence in
      Fig. 7A.

<400> SEQUENCE: 10
gaaactggac agcacagact tcaccggc    28

<210> SEQ ID NO 11

<211> LENGTH: 22
<212> TYPE: DNA
<213> ORGANISM: Artificial Sequence
<220> FEATURE:
<223> OTHER INFORMATION: Fragment obtained from cleavage of sequence in Fig. 7A.

<400> SEQUENCE: 11
gggagcactc cgacctagag tt                                              22

<210> SEQ ID NO 12
<211> LENGTH: 13
<212> TYPE: DNA
<213> ORGANISM: Artificial Sequence
<220> FEATURE:
<223> OTHER INFORMATION: Fragment obtained from cleavage of sequence in 7A.

<400> SEQUENCE: 12
cctgtcgtgt ctg                                                        13

<210> SEQ ID NO 13
<211> LENGTH: 11
<212> TYPE: DNA
<213> ORGANISM: Artificial Sequence
<220> FEATURE:
<223> OTHER INFORMATION: Fragment obtained from cleavage of sequence in 7A.

<400> SEQUENCE: 13
gtggtcgtgg t                                                          11

<210> SEQ ID NO 14
<211> LENGTH: 11
<212> TYPE: DNA
<213> ORGANISM: Artificial Sequence
<220> FEATURE:
<223> OTHER INFORMATION: Fragment obtained from cleavage of sequence in 7A.

<400> SEQUENCE: 14
gtggccgtgg t                                                          11

<210> SEQ ID NO 15
<211> LENGTH: 11
<212> TYPE: DNA
<213> ORGANISM: Artificial Sequence
<220> FEATURE:
<223> OTHER INFORMATION: Fragment obtained from cleavage of sequence in 7A.

<400> SEQUENCE: 15
tgtccctcgt g                                                          11